(12) United States Patent
Yoko et al.

(10) Patent No.: US 12,369,930 B2
(45) Date of Patent: Jul. 29, 2025

(54) SYSTEMS FOR GUIDED REAMING OF COMPLEX SHAPES

(71) Applicant: Zimmer, Inc., Warsaw, IN (US)

(72) Inventors: Tim Yoko, Granger, IN (US); Jeffery A. VanDiepenbos, New Paris, IN (US); Joseph Arthur Azbell, Roanoke, IN (US)

(73) Assignee: Zimmer, Inc., Warsaw, IN (US)

( * ) Notice: Subject to any disclaimer, the term of this patent is extended or adjusted under 35 U.S.C. 154(b) by 244 days.

(21) Appl. No.: 18/207,458

(22) Filed: Jun. 8, 2023

(65) Prior Publication Data

US 2023/0404603 A1 Dec. 21, 2023

Related U.S. Application Data

(60) Provisional application No. 63/434,593, filed on Dec. 22, 2022, provisional application No. 63/353,802, filed on Jun. 20, 2022.

(51) Int. Cl.
*A61B 17/16* (2006.01)
*A61F 2/46* (2006.01)
*A61F 2/30* (2006.01)

(52) U.S. Cl.
CPC .......... *A61B 17/164* (2013.01); *A61F 2/4684* (2013.01); *A61B 17/1668* (2013.01); *A61F 2002/30332* (2013.01)

(58) Field of Classification Search
CPC ............ A61B 17/1659; A61B 17/1668; A61B 17/1675; A61B 17/1764; A61B 17/164; A61F 2/4684; A61F 2/389
See application file for complete search history.

(56) References Cited

U.S. PATENT DOCUMENTS

| 4,822,362 A | 4/1989 | Walker et al. |
| 5,282,861 A | 2/1994 | Kaplan |

(Continued)

FOREIGN PATENT DOCUMENTS

| CN | 114869547 A | 8/2022 |
| CN | 118236202 A | 6/2024 |

(Continued)

OTHER PUBLICATIONS

"Australian Application Serial No. 2023203769, First Examination Report mailed May 16, 2024", 3 pgs.

(Continued)

*Primary Examiner* — Samuel S Hanna
(74) *Attorney, Agent, or Firm* — Schwegman Lundberg & Woessner, P.A.

(57) ABSTRACT

Systems and methods for reaming an intramedullary canal of a long bone comprise a trial stem configured to extend into the long bone along an insertion axis and a guide device comprising an adapter configured to couple to the trial stem and a reaming guidepost extending from the adapter along a guide axis, wherein the guide axis and the insertion axis are non-aligned. A method of reaming an intramedullary canal of a long bone to form a complex shaped socket can comprise inserting a stem into the intramedullary canal along an insertion axis, connecting a guide device to the stem, the guide device comprising a guidepost extending along a guide axis and guiding a cannulated reamer along the guidepost to remove bone from the intramedullary canal to form the complex shaped socket, wherein the guide axis and the insertion axis are non-aligned.

20 Claims, 29 Drawing Sheets

(56) References Cited

U.S. PATENT DOCUMENTS

| | | |
|---|---|---|
| 6,911,100 B1 | 6/2005 | Gibbs et al. |
| 7,291,174 B2 | 11/2007 | German et al. |
| 8,562,616 B2 | 10/2013 | May et al. |
| 8,721,733 B2 | 5/2014 | Bonitati |
| 8,758,444 B2 | 6/2014 | Wentorf et al. |
| 9,011,444 B2 | 4/2015 | Primiano et al. |
| 9,381,090 B2 | 7/2016 | Wentorf et al. |
| 9,737,408 B2 | 8/2017 | Leszko et al. |
| 10,213,215 B2 | 2/2019 | Servidio et al. |
| 10,265,083 B2 | 4/2019 | Servidio et al. |
| 10,524,806 B2 | 1/2020 | Collazo et al. |
| 10,596,009 B2 | 3/2020 | Mines et al. |
| 10,835,382 B2 | 11/2020 | Habegger et al. |
| 10,987,225 B2 | 4/2021 | Yoko et al. |
| 11,172,940 B2 | 11/2021 | Servidio et al. |
| 2003/0055509 A1 | 3/2003 | McCue et al. |
| 2003/0171756 A1 | 9/2003 | Fallin et al. |
| 2004/0267267 A1 | 12/2004 | Daniels et al. |
| 2009/0149964 A1 | 6/2009 | May et al. |
| 2010/0174378 A1 | 7/2010 | Metzger et al. |
| 2013/0024001 A1 | 1/2013 | Wentorf et al. |
| 2013/0131820 A1 | 5/2013 | Wentorf et al. |
| 2013/0150858 A1* | 6/2013 | Primiano ........... A61B 17/1764 623/20.35 |
| 2014/0214172 A1 | 7/2014 | Hood et al. |
| 2014/0277528 A1 | 9/2014 | Mines et al. |
| 2014/0277540 A1 | 9/2014 | Leszko et al. |
| 2015/0216667 A1 | 8/2015 | Monaghan |
| 2017/0000503 A1 | 1/2017 | Keefer et al. |
| 2018/0028324 A1 | 2/2018 | Clary et al. |
| 2019/0038417 A1 | 2/2019 | Yoko et al. |
| 2022/0061998 A1 | 3/2022 | Zappacosta et al. |
| 2022/0061999 A1 | 3/2022 | Zappacosta et al. |
| 2024/0207055 A1 | 6/2024 | Yoko et al. |
| 2024/0207056 A1 | 6/2024 | Yoko et al. |
| 2024/0207057 A1 | 6/2024 | Yoko et al. |
| 2024/0207058 A1 | 6/2024 | Yoko et al. |
| 2024/0207061 A1 | 6/2024 | Yoko et al. |
| 2024/0207062 A1 | 6/2024 | Yoko et al. |
| 2024/0207063 A1 | 6/2024 | Yoko et al. |

FOREIGN PATENT DOCUMENTS

| | | |
|---|---|---|
| CN | 118236203 A | 6/2024 |
| CN | 118236210 A | 6/2024 |
| CN | 118236211 A | 6/2024 |
| CN | 118285966 A | 7/2024 |
| EP | 1325718 A1 | 7/2003 |
| EP | 3127510 A1 | 2/2017 |
| EP | 4349281 A2 | 4/2024 |
| FR | 2949668 A1 | 3/2011 |
| JP | 2024000537 A | 1/2024 |
| JP | 2024091504 A | 7/2024 |
| JP | 2024091514 A | 7/2024 |
| JP | 2024091533 A | 7/2024 |
| JP | 2024091539 A | 7/2024 |
| JP | 2024091541 A | 7/2024 |
| JP | 2024091560 A | 7/2024 |

OTHER PUBLICATIONS

"Australian Application Serial No. 2023203769, Response filed Jul. 31, 2024 to First Examination Report mailed May 16, 2024", 15 pgs.

"European Application Serial No. 19819200.7, Summons to Attend Oral Proceedings mailed Jun. 25, 2024", 12 pgs.

"European Application Serial No. 23180479.0, Extended European Search Report mailed May 16, 2024", 14 pgs.

"European Application Serial No. 23180479.0, Partial Supplementary European Search Report mailed Feb. 16, 2024", 13 pgs.

"European Application Serial No. 23217988.7, Extended European Search Report mailed May 8, 2024", 7 pgs.

"European Application Serial No. 23217999.4, Extended European Search Report mailed May 8, 2024", 6 pgs.

"European Application Serial No. 23218009.1, Extended European Search Report mailed May 7, 2024", 10 pgs.

"European Application Serial No. 23218189.1, Extended European Search Report mailed May 8, 2024", 7 pgs.

"European Application Serial No. 23218191.7, Extended European Search Report mailed May 7, 2024", 7 pgs.

"European Application Serial No. 23218194.1, Extended European Search Report mailed May 10, 2024", 5 pgs.

"European Application Serial No. 23219853.1, Extended European Search Report mailed May 10, 2024", 5 pgs.

"Japanese Application Serial No. 2023-099994, Notification of Reasons for Refusal mailed May 14, 2024", w/ English Translation, 8 pgs.

Rodiger, Wolf, et al., "Flow-Join: Adaptive Skew Handling for Distributed Joins over High-Speed Networks", IEEE 32nd International Conference on Data Engineering (ICDE), Retrieved from the Internet: <https://db.in.tum.de/-roediger/papers/roediger2016flowjoin.pdf>, (2016), 1-12.

* cited by examiner

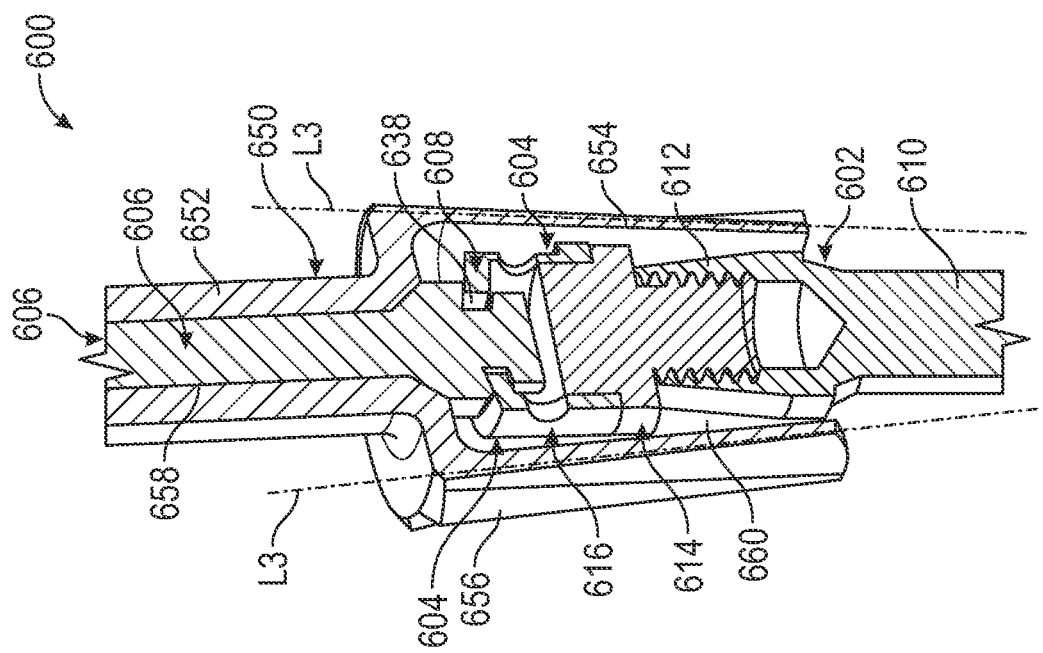

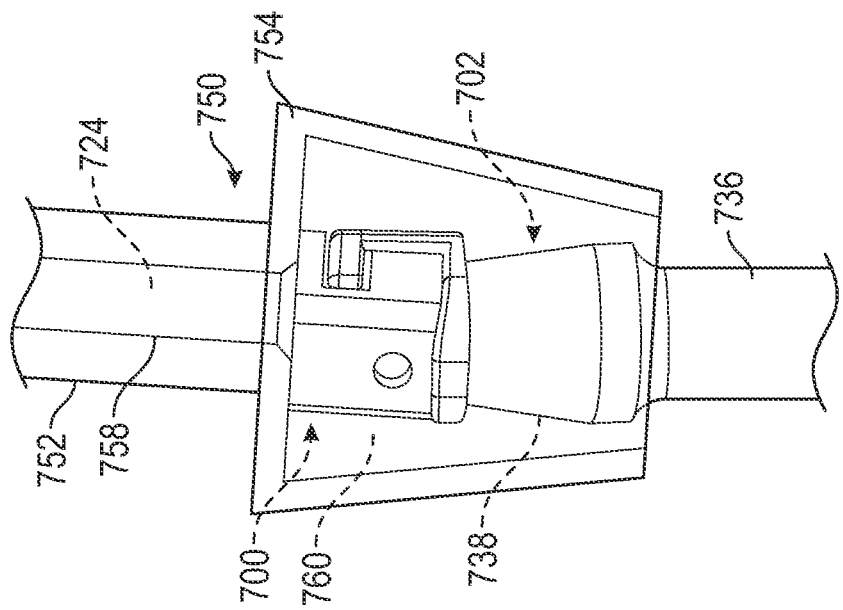
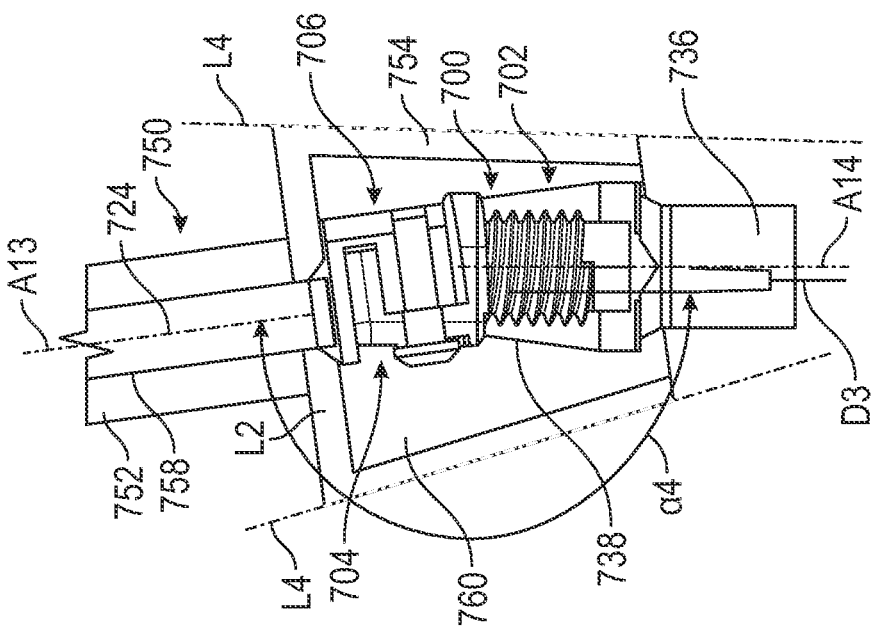
FIG. 23
FIG. 22

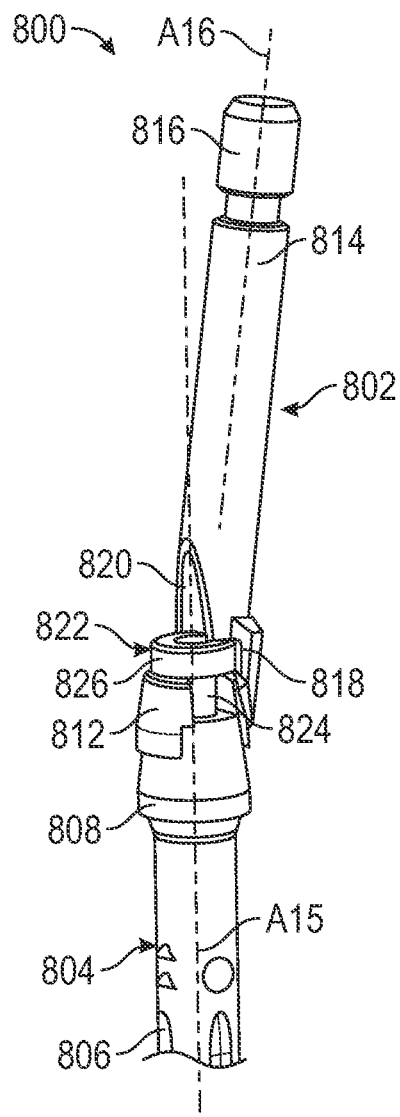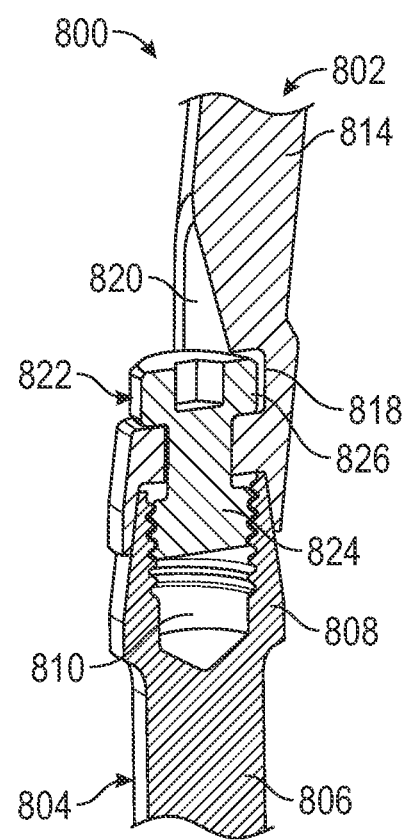
FIG. 24
FIG. 25

SYSTEMS FOR GUIDED REAMING OF COMPLEX SHAPES

CLAIM OF PRIORITY

This application claims the benefit of U.S. Provisional Patent Application Ser. No. 63/353,802, filed on Jun. 20, 2022, and also claims the benefit of U.S. Provisional Patent Application Ser. No. 63/434,593, filed on Dec. 22, 2022, the benefit of priority of which is claimed hereby, and which is incorporated by reference herein in its entirety.

TECHNICAL FIELD

This document pertains generally, but not by way of limitation, to prosthetic implant devices having stems configured to be inserted into bone. More specifically, but not by way of limitation, the present application relates to systems and methods of modifying bone to receive sleeves and cones that surround stems of tibial and femoral devices to facilitate attachment to bone when implanted.

BACKGROUND

Prosthetic implant devices, such as femoral and tibial components, sometimes include a stem extending from a bearing component such as a tibial tray. The stem can extend along a length of the diaphysis portion of the tibia, while the tray can be configured to abut a resected portion of the epiphysis portion of the tibia configured to mate with the femur. Sometimes the metaphysis portion of the tibia below the epiphysis includes damaged or unhealthy cancellous bone at the resection. As such, it is sometimes desirable to remove weakened bone material, such as with a broach or reamer, to leave a space in the metaphyseal portion of the bone larger than the stem. Sometimes a sleeve or cone is positioned in the space around a stem for the tibial or femoral component in order to facilitate attachment of the prosthesis to the bone.

Examples of sleeves and cones for use with prosthetic implants are described in U.S. Pat. No. 8,721,733 to Bonitati; U.S. Pat. No. 11,172,940 to Servidio et al.; U.S. Pub. No. 2014/0277528 to Mines et al.; U.S. Pub. No. 2014/0277540 to Leszko et al.; and U.S. Pub. No. 2017/0000503 to Keefer et al.

Overview

The present inventors have recognized, among other things, that problems to be solved in implanting prosthetic devices can include accurately reaming or otherwise modifying bone to receive a sleeve that attaches to a stem of a tibial or femoral component. Sleeves typically comprise a conical body or a conical-like body that is elongated in the medial-lateral direction. Some sleeves have symmetry in both the medial-lateral direction and the anterior-posterior direction such that a reamer can simply be inserted into the bone and then moved medial-laterally and anterior-posteriorly to make a space in the bone that mates with the sleeve. However, such reaming motions are sometimes performed freehand and can be difficult to execute.

Furthermore, the present inventors have recognized that symmetric sleeves do not always fit the anatomy of every patient and can sometimes remove too much healthy bone. It can, therefore, be desirable to use sleeves that have asymmetry, at least with respect to one anatomic plane. For example, the sleeve can be curved such that the anterior surface is convex, and the posterior surface is concave. As such, the sleeve can be symmetric about a sagittal plane, but asymmetric about a coronal plane. Furthermore, it can be desirable to angle the anterior wall of the sleeve relative to vertical differently than the angle of the posterior wall. As such, it can be difficult to use conventional reaming systems to freehand an asymmetric or partially-symmetric sleeve shape.

Previous systems to make shaped spaces with bone reamers have involved the use of a rig that can hold a reamer in a plurality of different positions. The rig can then be used to advance the reamer axially along a plurality of different linear paths. However, the shape of the sleeve is dictated by how the rig holds the reamer and the sleeve is thus limited to shapes made by axial insertion of the reamer. Such shapes may not adequately remove undesirable bone without also removing significant portions of healthy bone. In addition to being difficult to configure and set-up, such reaming rigs require multiple reaming steps to complete the reaming operation.

The present subject matter can help provide solutions to these problem, and other problems, by providing reaming systems that allow a reamer to be moved along trajectories that are offset, angled, or variable relative to an axis of the stem with which the cone or sleeve is to be used. The reaming system can be used to produce symmetric, partially symmetric, asymmetric, offset and non-aligned spaces, as well as other complex shaped spaces, for receiving a correspondingly shaped sleeve or cone. In examples, complex shaped sockets can comprise pockets that are shaped differently than the reamer or differently than a cross-section of the reamer. The reamer can be slid along a guidepost that restricts movement of the reamer in various directions. The guidepost can be pivoted at a hinge connected to a trial stem so as to allow the reamer to sweep along a vertical reaming plane. The guidepost can be articulated at a ball joint connected to a trial stem so as to allow the reamer to be swept through a horizontal reaming envelope.

In an example, a system for reaming an intramedullary canal of a long bone can comprise a trial stem configured to extend into the long bone along an insertion axis and a guide device comprising an adapter configured to couple to the trial stem and a reaming guidepost extending from the adapter along a guide axis, wherein the guide axis and the insertion axis are non-aligned.

In another example, a method of reaming an intramedullary canal of a long bone to form a complex shaped socket can comprise inserting a stem into the intramedullary canal along an insertion axis, connecting a guide device to the stem, the guide device comprising a guidepost extending along a guide axis and guiding a cannulated reamer along the guidepost to remove bone from the intramedullary canal to form the complex shaped socket, wherein the guide axis and the insertion axis are non-aligned.

In an example, a system for reaming an intramedullary canal of a long bone can comprise a trial stem configured to extend into the long bone along an insertion axis and a guide device comprising an adapter configured to couple to the trial stem and reaming guidepost extending from the adapter along a guide axis, wherein the guide axis and the insertion axis are non-aligned.

In an additional example, a method of reaming an intramedullary canal of a long bone to form a complex shaped socket can comprise inserting a stem into the intramedullary canal along an insertion axis, connecting a guide device to the stem, the guide device comprising a guidepost extending along a guide axis and guiding a cannulated reamer along the guidepost to remove bone from the intramedullary canal to form the complex shaped socket, wherein the guide axis and the insertion axis are non-aligned.

In another example, a system for reaming an intramedullary canal of a long bone can comprise a trial stem configured to extend into the long bone along an insertion axis and a guide device comprising an adapter configured to couple to the trial stem, a reaming guidepost extending from the adapter along a guide axis and a pivoting coupler connecting the reaming guidepost to the adapter, wherein the pivoting coupler produces a projected pivot point along the insertion axis spaced longitudinally from the adapter.

In a further example, a method of reaming an intramedullary canal of a long bone to form a complex shaped socket can comprise inserting a stem into the intramedullary canal along an insertion axis, connecting a guide device to the stem, the guide device comprising a guidepost extending along a guide axis, guiding a cannulated reamer along the guidepost to remove bone from the intramedullary canal to form the complex shaped socket and pivoting the guidepost relative to the stem with the cannulated reamer, wherein a projected pivot point along the insertion axis spaced longitudinally from the guide device along the insertion axis.

In yet another example, a system for reaming an intramedullary canal of a long bone can comprise a trial stem configured to extend into the long bone along an insertion axis, an angled stem extension comprising, a shaft and a coupler configured to rotatably attach the shaft to the trial stem at an angle to the insertion axis, and a fastener for selectively locking rotation of the angled stem extension relative to the trial stem.

In yet an additional example, a method of reaming an intramedullary canal of a long bone to form a bone pocket can comprise inserting a stem into the intramedullary canal along an insertion axis, orienting an angled stem extension post relative to the stem, attaching a template to the angled stem extension post, rotating the template along with the angled stem extension to align the template with anatomic features of the long bone, locking a rotational position of the angled stem extension post relative to the stem, removing the template, and reaming the intramedullary canal along the angled stem extension.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

FIG. 18 is a cross-sectional view of the articulating guide device of FIGS. 16A-17 showing arcuate guide paths and a virtual center of rotation.

FIG. 19A is a cross-sectional view of a reamer positioned around the guidepost of the articulating guide device of FIG. 16A.

FIG. 22 is a side view of the articulating guide device of FIGS. 20A-21B.

FIG. 23 is a perspective view of the articulating guide device of FIG. 20A with a reamer shown in phantom over the articulating guide device.

FIG. 24 is a perspective view of an angled stem extension post attached to a trial stem in a rotatable manner with a fastener.

FIG. 25 is a cross-sectional view of the lock-down angled stem extension post and trial stem of FIG. 24 showing the fastener inserted into a socket of the trail stem.

Figure 1:
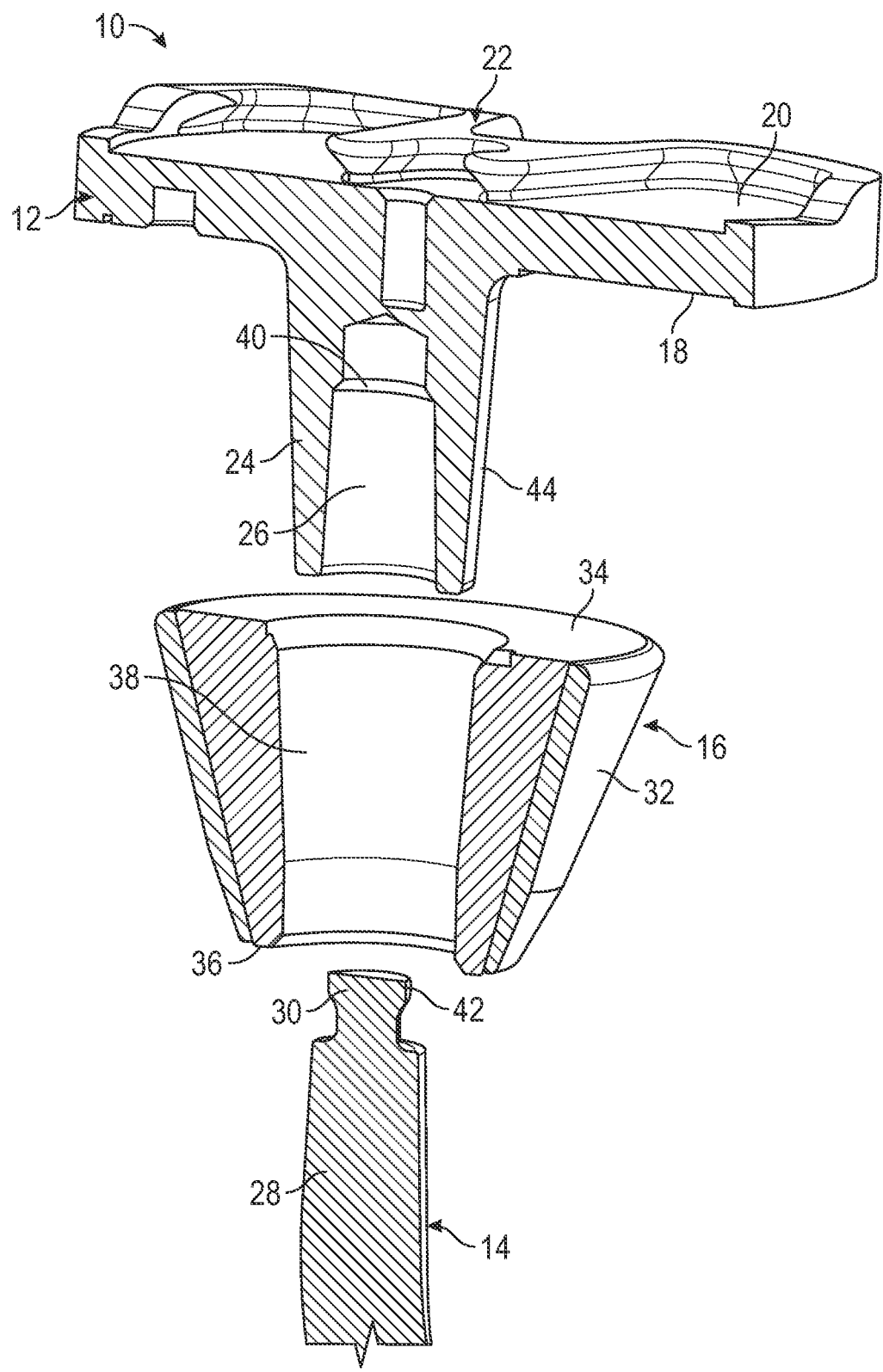
FIG. 1 is an exploded perspective view of a tibial component having a tibial stem with a sleeve configured to be disposed to surround the tibial stem housing.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

FIG. 1 is an exploded perspective view of tibial construct or tibial component 10 having tibial tray 12, tibial stem 14 and sleeve 16. Tibial tray 12 can comprise bone-facing surface 18, bearing surface 20, retaining features 22, stem housing 24 and stem housing socket 26. Tibial stem 14 can comprise shaft portion 28 and lockdown post 30. Sleeve 16 can comprise exterior surface 32, proximal portion 34, distal portion 36 and interior channel 38.

Figure 4:
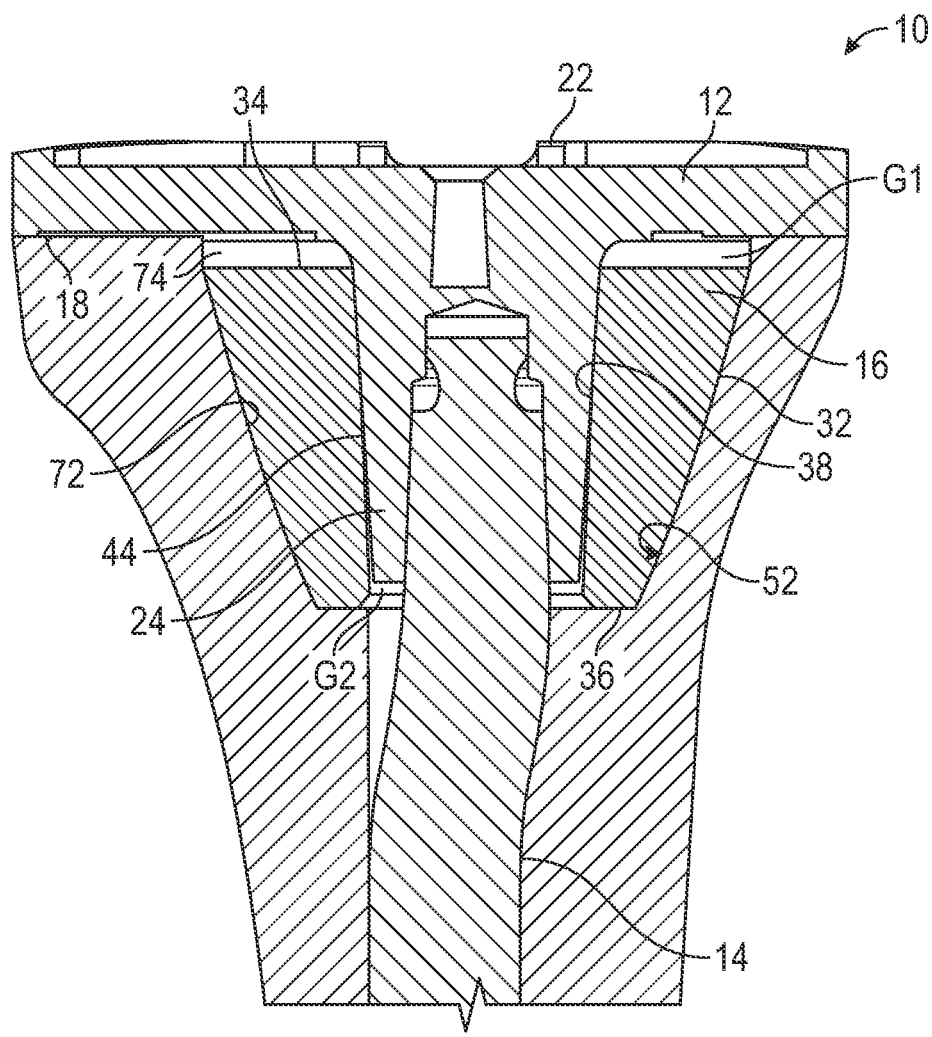
FIG. 4 is a side cross-sectional view of the tibial component and sleeve of FIG. 1 inserted into the reamed intramedullary canal of FIG. 3 in a coupled configuration.

Tibial stem 14 is configured to be attached to tibial tray 12 and sleeve 16 is configured to surround tibial stem 14 and stem housing 24. Lockdown post 30 of tibial stem 14 can be inserted into stem housing socket 26 of tibial tray 12. Stem housing socket 26 can include lip 40 that can engage head 42 of lockdown post 30 to hold tibial stem 14 within stem housing socket 26. Outer surface 44 of stem housing 24 and interior channel 38 of sleeve 16 can be configured to engage each other to secure sleeve 16 to tibial tray 12. In examples, outer surface 44 can be configured to have a Morse taper and interior channel 38 can be configured to have a corresponding shape to seat on the Morse taper of outer surface 44, as shown in FIG. 4. Retaining features 22 can be used to secure various bearing components against bearing surface 20 of tibial component 10 to engage a femoral component. For example, retaining features 22 can include flanges having lips into which mating components of mobile or fixed bearings can be fitted to engage condylar surfaces of a femoral component.

Tibial stem 14 is configured to be pushed down into an intramedullary canal of a tibia bone to anchor tibial tray 12 so that bone-facing surface 18 contacts a resected bone surface of the tibia. Furthermore, sleeve 16 can be positioned around stem housing 24 to provide additional anchoring. For example, tibial stem 14 can be inserted into one or both of cancellous and cortical bone and sleeve 16 can be pushed into engagement with one or both of cancellous and cortical bone. Exterior surface 32 can be porous to promote bone in-growth, as is known in the art. The systems, devices and methods of the present disclosure can allow for the use of sleeves or cones that have asymmetric or partially-symmetric shapes to be implanted into a long bone to better match anatomic shapes, remove undesirable bone and preserve healthy bone. The various reaming systems, devices and methods described herein can produce bone pockets having complex shapes, including irregular, varied, offset, non-aligned, partially-symmetric or asymmetric geometries, that can receive sleeves or cones having a corresponding shape or another shape. Such shapes can encompass shapes that are better contoured to match with anatomy of a general patient population. In examples, patient-specific bone pockets can be produced with the systems, devices and methods described herein.

Figure 2:
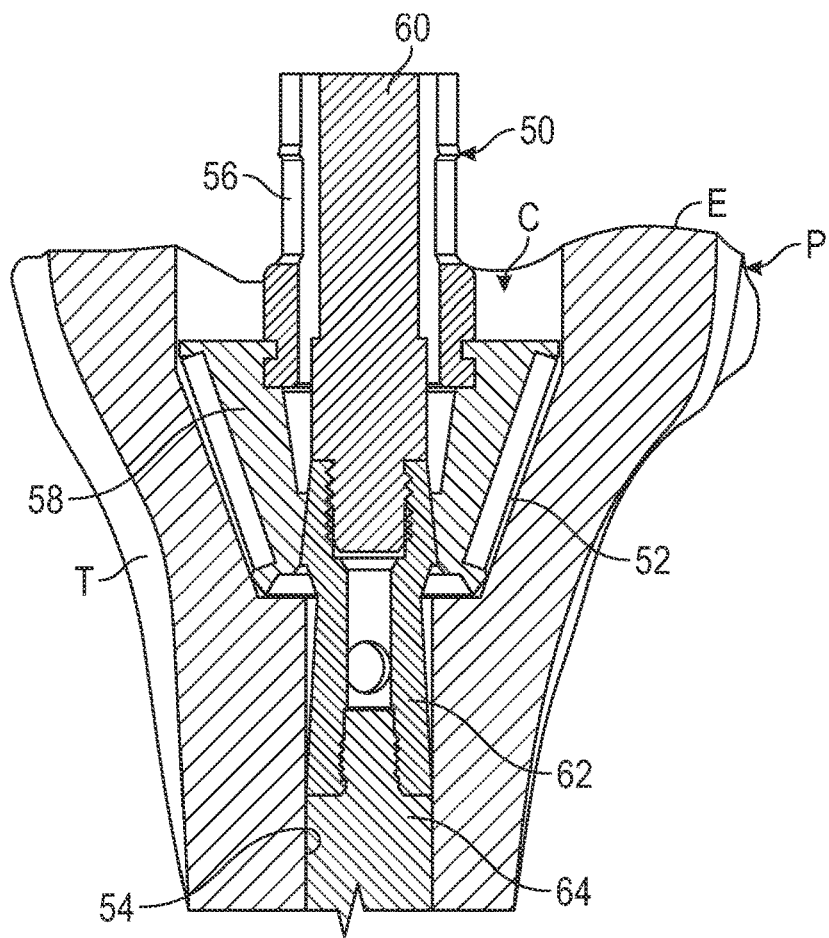
FIG. 2 is a side cross-sectional view of a proximal end of a tibia having a reaming tool inserted into the metaphysis via the intramedullary canal of the tibia to form a reamed channel.

FIG. 2 is a side cross-sectional view of proximal end P of tibia T having reaming tool 50 inserted into metaphysis region of tibia T along an axis extending along intramedullary canal C of tibia T to form reaming channel 52. Reaming channel 52 can intersect stem channel 54, which can also extend along the axis of intramedullary canal C. Reaming tool 50 can comprise reamer shaft 56 and reaming head 58. Reamer shaft 56 and reaming head 58 can be cannulated to include an internal passage that receives stem extension post 60, which is connected to stem provisional 62 and extension post 64. Stem extension post 60 and extension post 64 can be coaxially aligned and fixed relative to each other. In other embodiments, stem provisional 62 and extension post 64 can be combined into a single piece.

With reaming head 58 inserted into tibia T, reamer shaft 56 can be reciprocated in an up-and-down motion relative to the orientation of FIG. 1 to widen reaming channel 52 along the axis of intramedullary canal C. As shown in FIG. 2, reaming head 58 can include various cutting surfaces, serrations, teeth, lands, edges or the like to chip away, cut away or otherwise remove bone. In embodiments, reaming head 58 can be inserted into reaming channel 52 to widen stem channel 54 into reaming channel 52. Stem channel 54 can be produced using a broach or a reamer in any suitable manner before or after reaming tool 50 is used to form reaming channel 52.

Stem channel 54 can comprise a generally cylindrical shaped passage extending longitudinally along an axis of tibia T. Stem channel 54 can extend into and through cancellous bone of tibia T. The cancellous bone of tibia T is surrounded by an outer layer of harder cortical bone. Stem channel 54 can form a passage for receiving a tibial post or stem that extends from a tibial component. For example, stem provisional 62 and extension post 64 can be inserted into stem channel 54. Furthermore, tibial stem 14 of FIG. 1 can be inserted into stem channel 54 after trialing and straight or offset stem provisional 62 and extension post 64 are removed. Tibial stem 14 can provide anchoring of tibial component 10 to tibia T.

Figure 3:
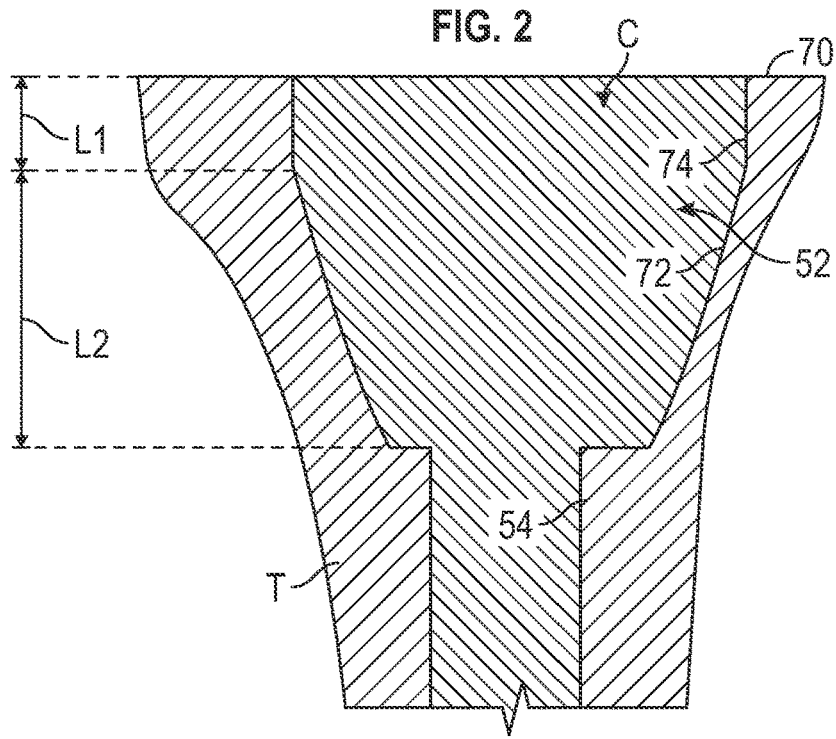
FIG. 3 is a side cross-sectional view of the proximal end of the tibia of FIG. 2 with the reaming tool removed and an epiphysis region of the bone resected at a resected surface.

Tibial component 10 can be further anchored to tibia T using sleeve 16 of FIG. 1. Reaming channel 52 can comprise a widened and tapered portion of stem channel 54 shaped to receive sleeve 16. Reaming head 58 can have the same outer angular dimensions as sleeve 16. That is, the angles of the side walls relative to the inferior and superior wall can be the same. As shown in FIG. 3, the shape of reaming channel 52 is typically symmetric to accommodate a similarly shaped sleeve 16. For example, the anterior-posterior thickness of sleeve 16 can be uniform in the central portion of the device. Additionally, the slope on the anterior and posterior walls can be the same. With the present disclosure, sleeves or cones having non-uniform thicknesses or differently sloped sidewall can be used.

FIG. 3 is a side cross-sectional view of the proximal end of tibia T of FIG. 2 with reaming tool 50 removed and epiphysis end E of tibia T resected at resected surface 70. Reaming channel 52 can include tapered portion 72 and longitudinal portion 74. Longitudinal portion 74 can have length L1, which can be measured from resected surface 70. In other words, tapered portion 72 can begin a distance equal to length L1 below resected surface 70. Tapered portion 72 can have a longitudinal length L2 equivalent to the height of reaming head 58. Additionally, the angle between longitudinal portion 74 and tapered portion 72 can match with the geometry of reaming head 58. After reaming with reaming head 58, epiphysis E is resected to provide a planar, or nearly planar, surface for engaging flush with tibial tray 12 (FIG. 1) at resected surface 70. Additionally, re-sectioning of tibia T can be performed prior to reaming. Note, longitudinal portion 74 typically results from reaming tool 50 being advanced in a straight superior-inferior direction. With the reaming systems of the present disclosure, longitudinal portion 74 can be eliminated, partially or fully, by the introduction of pivoting and articulating between stem extension post 60 and stem provisional 62.

FIG. 4 is a side cross-sectional view of tibial component 10 and sleeve 16 of FIG. 1 inserted into reamed intramedullary canal C of FIG. 3. In the configuration of FIG. 4, sleeve 16 is attached to stem housing 24. Sleeve 16 can be attached to stem housing 24 in a variety of configurations, such as via threaded engagement, ribbed coupling (e.g., where shallow ribs on stem housing 24 engage with shallow ribs on sleeve 16), snap fit, force fit, press fit, Morse taper, or via use of additional fasteners. In the illustrated embodiment, sleeve 16 is attached to stem housing 24 via Morse taper. In examples, outer surface 44 of stem housing 24 is configured to have a Morse taper and interior channel 38 of sleeve 16 is configured to have a mating recess such that a self-holding connection is made. Such a configuration is discussed in greater detail in U.S. Pat. No. 6,911,100 to Gibbs et al., which is hereby incorporated by reference in its entirety for all purposes. In other examples, other tapered connections can be used, such as described in U.S. Pub. No. 2015,0216667 to Monaghan, which is hereby incorporated by reference in its entirety for all purposes. In yet other examples, sleeve 16 can be coupled to bone-facing surface 18 rather than stem housing 24.

With sleeve 16 connected to stem housing 24, sleeve 16 contacts tibia T at tapered portion 72 of reaming channel 52. Longitudinal portion 74 is small to permit exterior surface 32 to engage tapered portion 72 while still allowing gap G1 to be present between bone-facing surface 18 of tibial tray 12 and proximal portion 34 of sleeve 16. Gap G1 can be filled with bone cement. For example, gap G1 and reaming channel 52 can be filled with bone cement prior to insertion of tibial stem 14 into reaming channel 52. This can permit gap G2 along distal portion 36 to fill with bone cement.

Sleeve 16 can be attached to stem housing 24 in a coupled configuration as discussed. Sleeve 16 can additionally be inserted into reamed intramedullary canal C of FIG. 3 in an uncoupled configuration. As such, sleeve 16 can be not attached to stem housing 24. In such a configuration (e.g., unattached to stem housing 24), sleeve 16 can be referred to as a cone.

In either case, it can be desirable to have exterior surface 32 closely conform to walls of a bone pocket reamed or otherwise formed into a bone in order to, among other things, facilitate bone growth into sleeve 16. Rather than having a simple cylindrical shaped sleeve, conical shaped sleeve or a symmetric oblong sleeve, it can be desirable to have curved, partially-symmetric or asymmetric sleeves so that more diseased bone can be removed from a medial or lateral side of the intramedullary canal without removing healthy bone on the opposite side. The systems, devices and methods of the present disclosure facilitate production of different shaped bone pockets. FIGS. 1-4 are discussed with reference to reaming a tibia. However, the systems, devices and methods of the present disclosure can be used in other bones, particularly other long bones, such as femurs.

Figure 5:
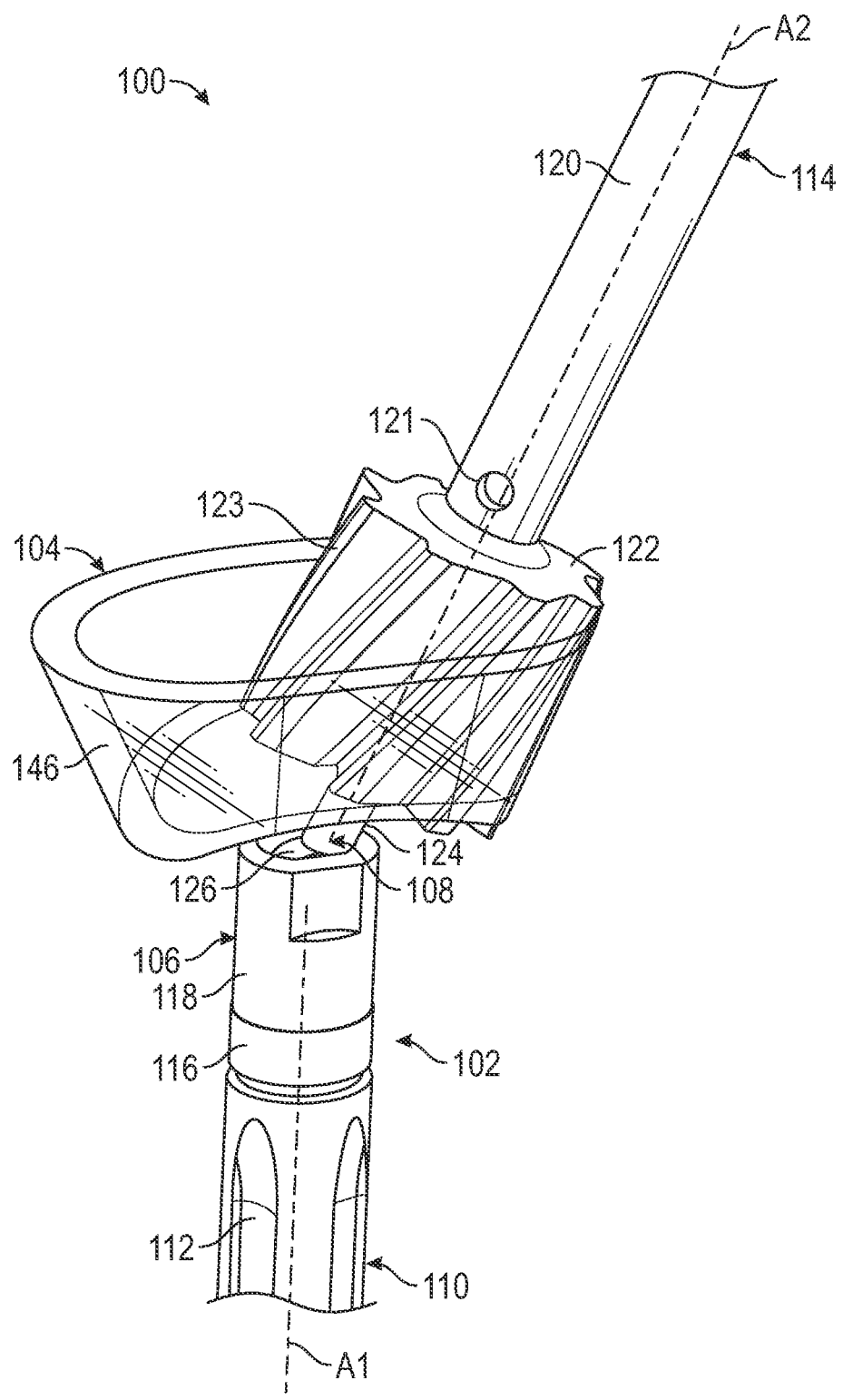
FIG. 5 is a perspective view of a reaming system comprising an articulating guidepost configured to produce complex shaped sleeve pockets, including symmetric and asymmetric sleeve pockets.

FIG. 5 is a perspective view of reaming system 100 comprising articulating guide device 102 configured to produce bone pockets (e.g., spaces within bone), or sleeve sockets, that can accept uniformly shaped, partially-symmetric or asymmetrically shaped sleeves, as illustrated by bone-removal envelope 104. Articulating guide device 102 can comprise cap 106 and guidepost 108. Articulating guide device 102 can couple to trial stem 110, which can comprise elongate body 112. Cannulated reamer 114 can slide along guidepost 108. Cap 106 can comprise coupler 116 and limiter 118. Cannulated reamer 114 can comprise cannulated shaft 120, which can include window 121, and cannulated cutter 122, which can include teeth 123. Guidepost 108 can comprise stem 124 and ball 126.

Trial stem 110 can be implanted into an intramedullary canal of a long bone, similarly as tibial stem 14 of FIGS. 1-4. Trial stem 110 can be configured to extend along insertion axis A1. Articulating guide device 102 can couple to trial stem 110. Stem 124 of guidepost 108 can extend along reaming axis A2. Ball 126 of guidepost 108 can allow stem 124 to articulate in a multi-directional fashion so that cannulated reamer 114 can be moved not only in a superior-inferior direction along stem 124, but in a transverse plane encompassing anterior-posterior and medial-lateral angulation. Limiter 118 of cap 106 can control, e.g., limit, movement of stem 124 so that cannulated cutter 122 can produce bone-removal envelope 104 of a desired shape.

Figure 6:
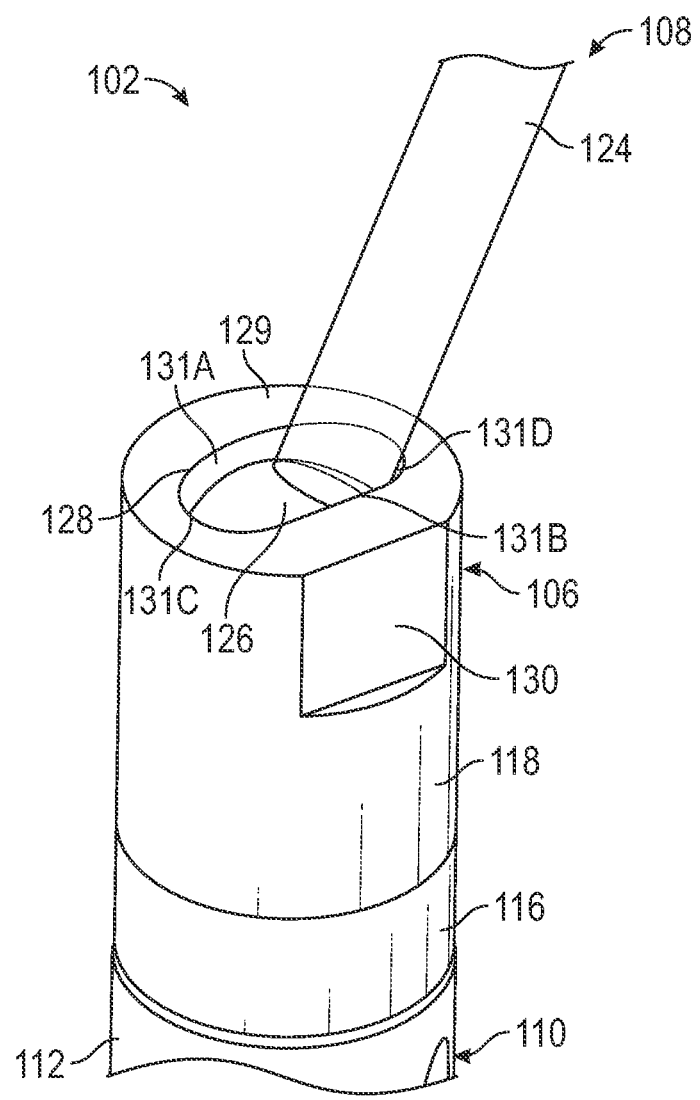
FIG. 6 is a perspective view of the articulating guidepost of FIG. 5 coupled to a trial stem via a cap including a bone-removal template.
Figure 7:
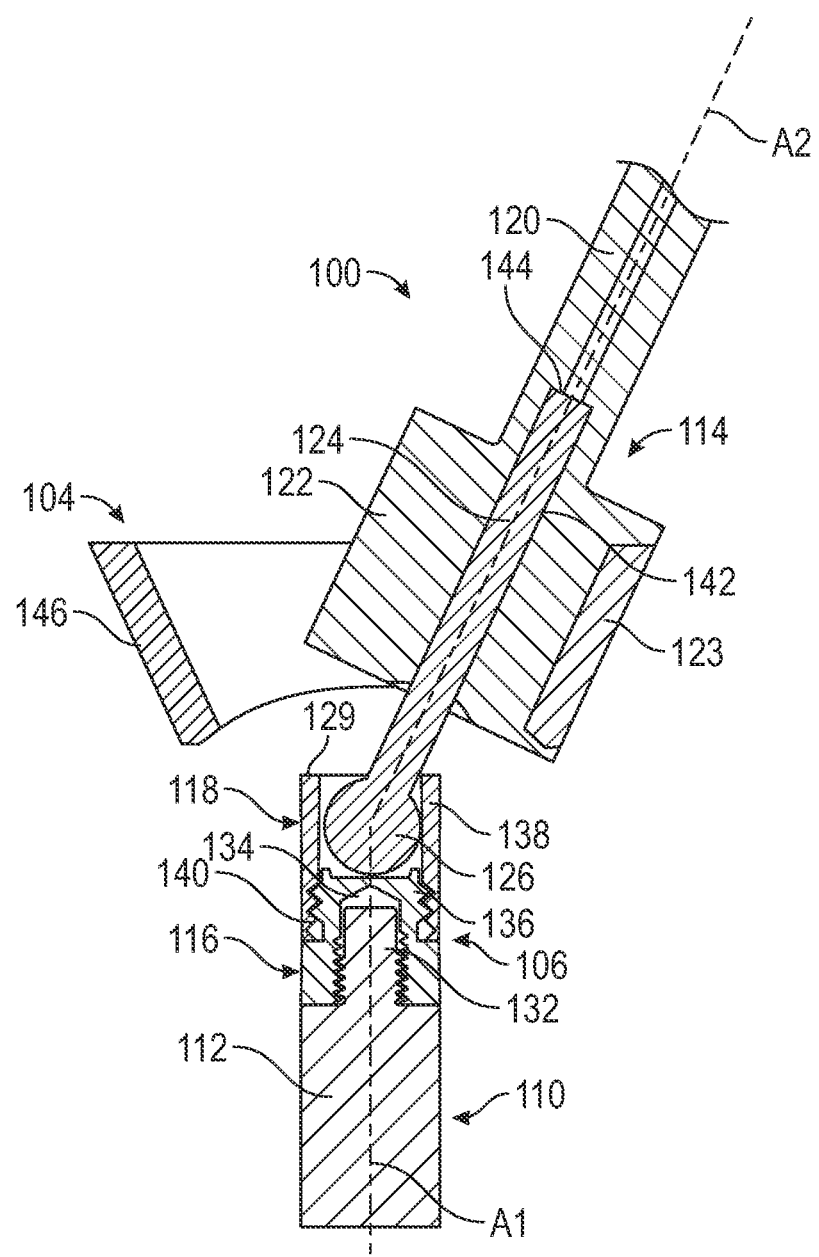
FIG. 7 is a side cross-sectional view of the reaming system of FIG. 5 showing a cannulated reamer moveable about a bone-removal envelope to produce a complex shaped sleeve pocket.

FIG. 6 is a perspective view of the articulating guide device 102 of FIG. 5 coupled to trial stem 110 via cap 106. Cap 106 can comprise coupler 116 and limiter 118. Guidepost 108 can comprise stem 124 and ball 126. Limiter 118 can comprise bone-removal template 128, upper surface 129 and torque face 130. Coupler 116 can be attached to elongate body 112 of trial stem 110 via a threaded engagement and limiter 118 can be attached to coupler 116 via a threaded engagement to retain guidepost 108, as shown in FIG. 7. Ball 126 can be retained within limiter 118 via upper surface 129 of limiter 118. Ball 126 can permit stem 124 to multi-directionally articulate to allow cannulated reamer 114 to change orientation relative to trial stem 110 such that axis A2 (FIG. 1) can change angles relative to axis A1.

Bone-removal template 128 can comprise a shape to which a cross-section of a bone pocket is made to receive a sleeve or cone. In the illustrated example, bone-removal template 128 can have curved front wall 131A, straight back wall 131B, curved side wall 131C and curved side wall 131D. Curved front wall 131A can be configured to face in the anterior direction and extend proximate a cortical bone wall at an anterior of a tibial plateau and straight back wall 131B can be configured to face in the posterior direction and extend proximate a cortical bone wall at a posterior of a tibial plateau. However, bone-removal template 128 can have other shapes. Walls 131A-131D can limit movement of stem 124, and therefore cannulated reamer 114, so that cutter 122 produces bone-removal envelope 104.

FIG. 7 is a side cross-sectional view of reaming system 100 of FIG. 5 showing cannulated reamer 114 moveable about bone-removal envelope 104 to produce a complex shaped sleeve socket. Trial stem 110 can comprise elongate body 112 and coupling head 132. Coupler 116 can comprise socket 134 and coupling head 136. Limiter 118 can comprise sidewall 138 and internal threads 140. Cannulated reamer 114 can comprise shaft 120, cutter 122, guide channel 142 and end stop 144.

Coupler 116 and limiter 118 can be assembled to capture ball 126 such that stem 124 protrudes from bone-removal template 128. External threading on coupling head 136 can be engaged with internal threads 140 on sidewall 138. Sidewall 138 can be shaped to retain ball 126 against coupler 116. For example, sidewall 138 can be increase in thickness at upper surface 129, such as by having a flange or being tapered. Coupler 116 can be attached to trial stem 110. External threading on coupling head 132 of elongate body 112 can be engaged with internal threads within socket 134 of coupler 116.

Assembled as such, cannulated reamer 114 can be moved axially along axis A2 by sliding up and down along stem 124 to control the depth of bone-removal envelope 104. The depth of cannulated reamer 114 can be controlled by the length of stem 124 and the position of end stop 144. For example, stem 124 can be longer than guide channel 142 to prevent cannulated reamer 114 from engaging articulating guide device 102. Stem 124 can be viewed through window 121 (FIG. 5) so a user can verify proper assembly of cannulated reamer 114 with articulating guide device 102.

Additionally, cannulated reamer 114 can be articulated by rotating ball 126 within limiter 118 to cause changes in the angle between axis A1 and axis A2. As discussed with reference to FIG. 8, the extent that cannulated reamer can be angled in the anterior-posterior direction, medial-lateral direction and directions in-between is controlled by the shape of template 128. The greater the amount of articulation, e.g., the greater the angle between axis A1 and axis A2, the greater the angle of the surface of bone-removal envelope 104 in the direction of the angulation with a corresponding reduction in the angle of the surface of bone-removal envelope 104 in the direction away from the angulation. However, stem 124 can be angled in a three-hundred-sixty-degree range of motion relative to axis A1 such that the slope of the walls of bone-removal envelope 104 can be controlled in any direction.

Figure 8:
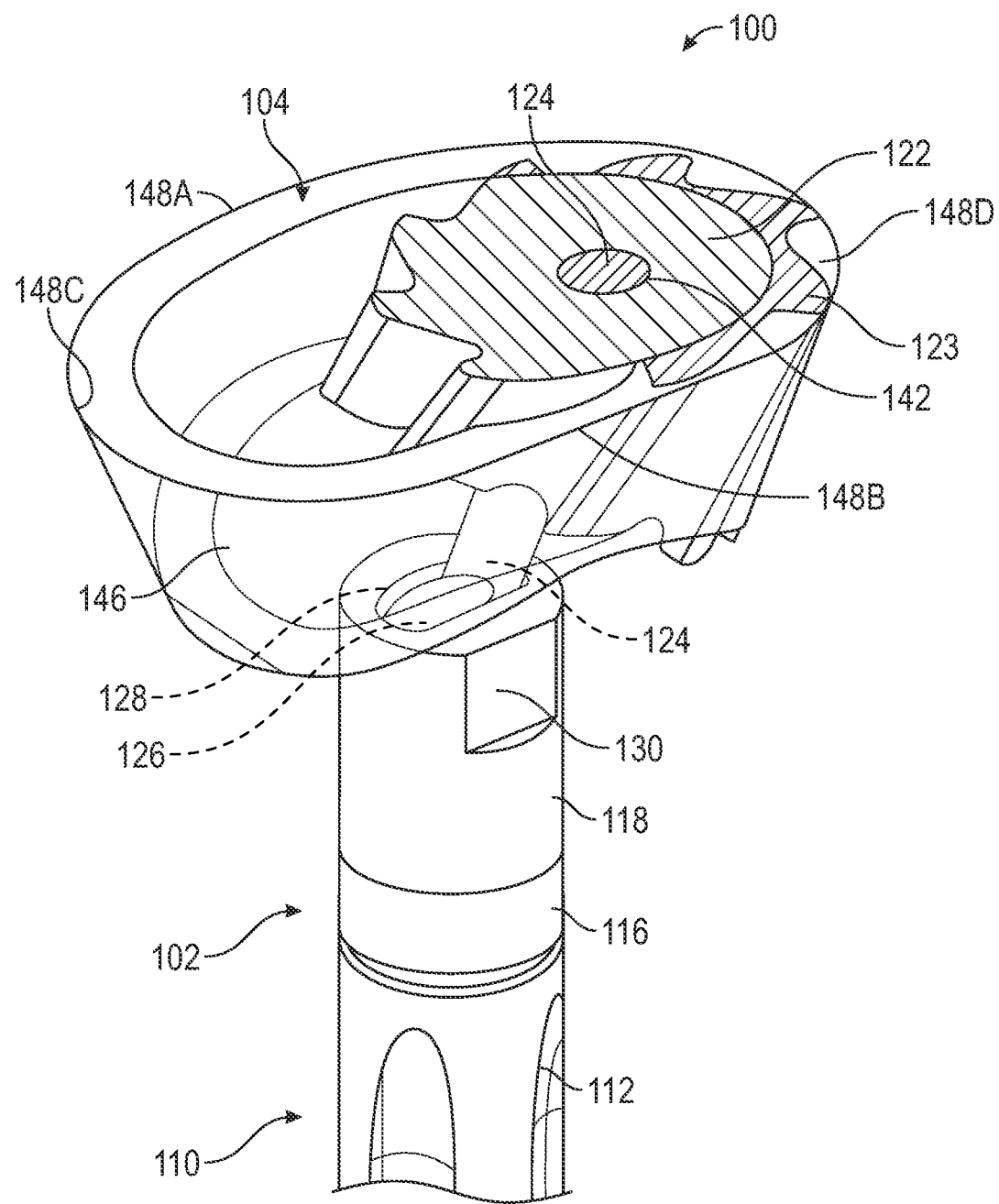
FIG. 8 is a perspective cross-sectional view of the bone-removal envelope of FIG. 7 showing the bone-removal envelope relative to the bone-removal template.

FIG. 8 is a perspective cross-sectional view of reaming system 100 of FIG. 5 showing bone-removal envelope 104 relative to bone-removal template 128. Bone-removal envelope 104 can have outer wall 146 comprising curved front wall 148A, straight back wall 148B, curved side wall 148C and curved side wall 148D. Curved wall 148A can be configured to face in the anterior direction and straight wall 148B can be configured to face in the posterior direction. Bone-removal envelope 104 can have a shape that is the inverse of a shape of a sleeve socket reamed within bone and that corresponds to the shape of a sleeve to be inserted in the sleeve socket. Bone-removal envelope 104 can correspond to the shape of a sleeve or cone to be implanted into the sleeve socket.

Teeth 123 of cannulated cutter 122 can engage with bone matter to produce envelope 104. The outer radial extent of teeth 123 can produce outer wall 146 as cannulated reamer 114 is articulated about ball 126. Ball 126 can allow stem 124 to be moved side-to-side and front-to-back or in circular motions to remove bone. Bone-removal template 128 can limit movement of stem 124 so that the shape of outer wall 146 matches the shape of bone-removal template 128, but on a larger scale.

Reaming system 100 of FIGS. 5-8 can be used to produce complex shaped bone pockets to receive correspondingly or similarly shaped sleeves and cones. The complex shaped bone pockets can be produced in a single reaming step. The complex shaped bone pockets can have different shapes on medial and lateral portion and anterior and posterior portions of the bone pocket.

Figure 9A:
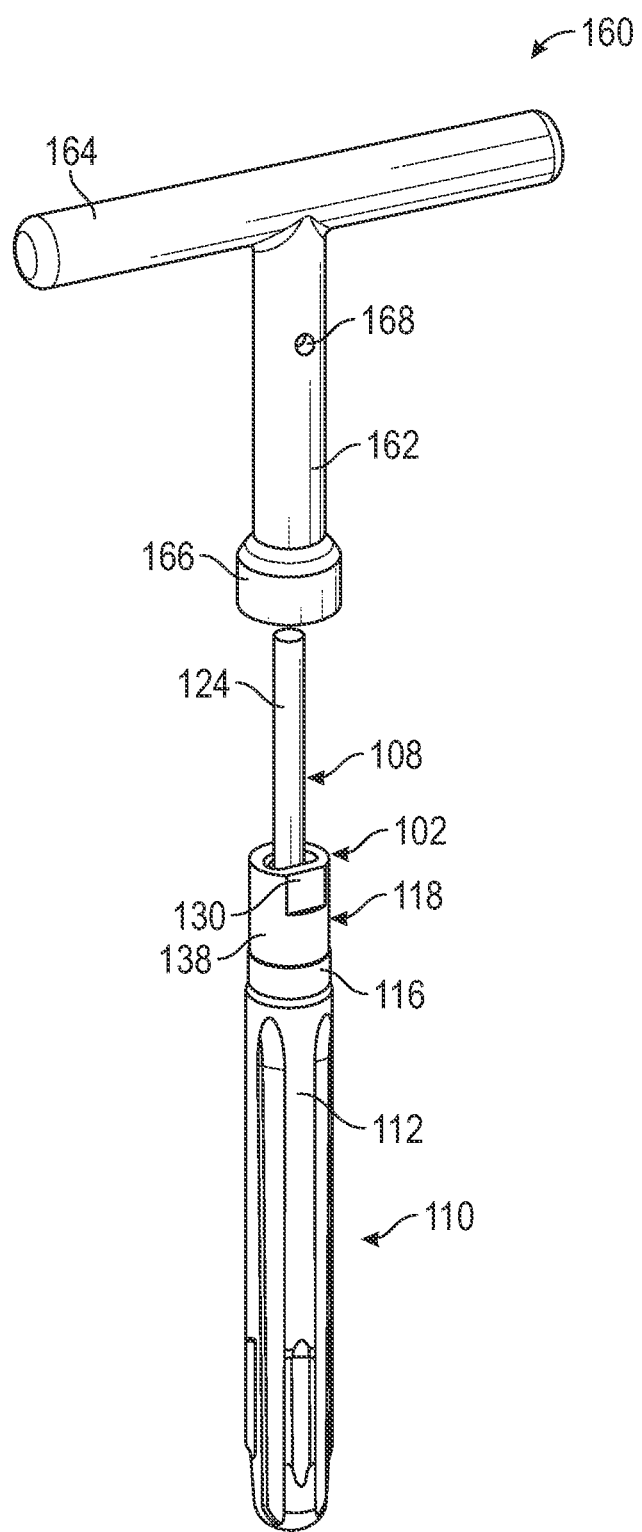
FIG. 9A is a perspective exploded view of an insertion tool for inserting the trial stem of FIG. 5 into bone via attachment to the cap of FIG. 6.
Figure 9B:
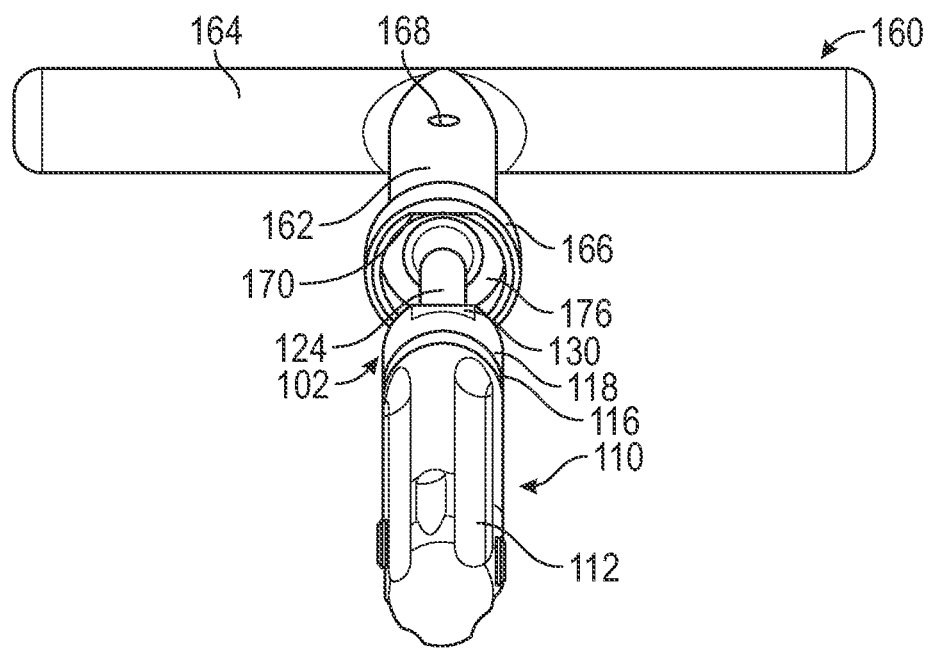
FIG. 9B is a perspective bottom view of the insertion tool of FIG. 9A showing a shoulder for engaging a feature of the cap.
Figure 9C:
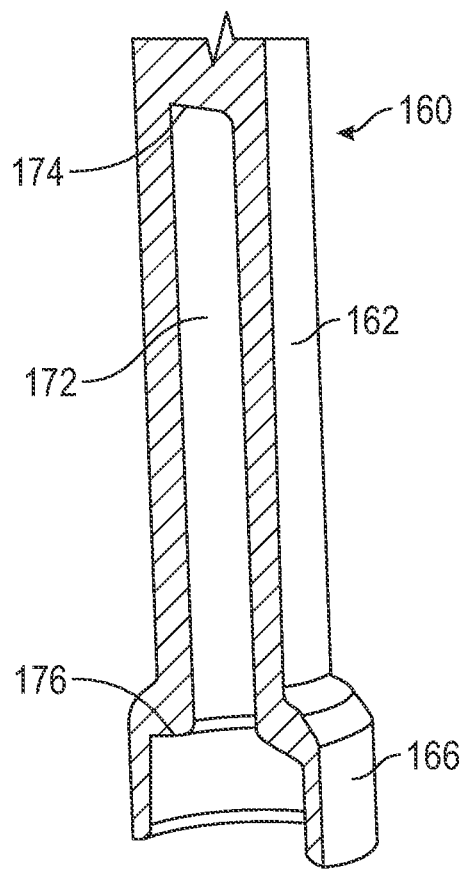
FIG. 9C is a partial cross-sectional view of the insertion tool of FIGS. 9A and 9B showing a channel for receiving the guidepost.

FIG. 9A is a perspective exploded view of insertion tool 160 for inserting trial stem 110 into bone via attachment to limiter 118. Insertion tool 160 can comprise shaft 162, handle 164, collar 166 and window 168. FIG. 9B is a perspective bottom view of insertion tool 160 of FIG. 9A showing shoulder 170 for engaging torque face 130 of limiter 118. FIG. 9C is a cross-sectional view of insertion tool 160 of FIGS. 9A and 9B showing channel 172 having end face 174. FIGS. 9A-9C are discussed concurrently.

After articulating guide device 102 is attached to trial stem 110, insertion tool 160 can be attached to articulating guide device 102. Stem 124 can be inserted into channel 172 and shaft 162 can be slid down around stem 124 until collar 166 engages sidewall 138 of limiter 118. In particular, sidewall 138 of limiter 118 can be inserted into counterbore 176 within collar 166 so that torque face 130 engages shoulder 170. The tip of stem 124 can be viewed in window 168 to allow a user to know that insertion tool 160 is fully seated on limiter 118. Engagement of torque face 130 and shoulder 170 can allow torque applied to shaft 162, such as from handle 164, can be transmitted to limiter 118. As such, insertion tool 160 can be used to push trial stem 110 down into bone or can be used to attach articulating guide device 102 to trial stem 110 already inserted into bone. As discussed with reference to FIG. 10, various features of insertion tool 160 or attachments thereto can be used to align insertion tool 160, and articulating guide device 102 therein, with anatomy.

Figure 10:
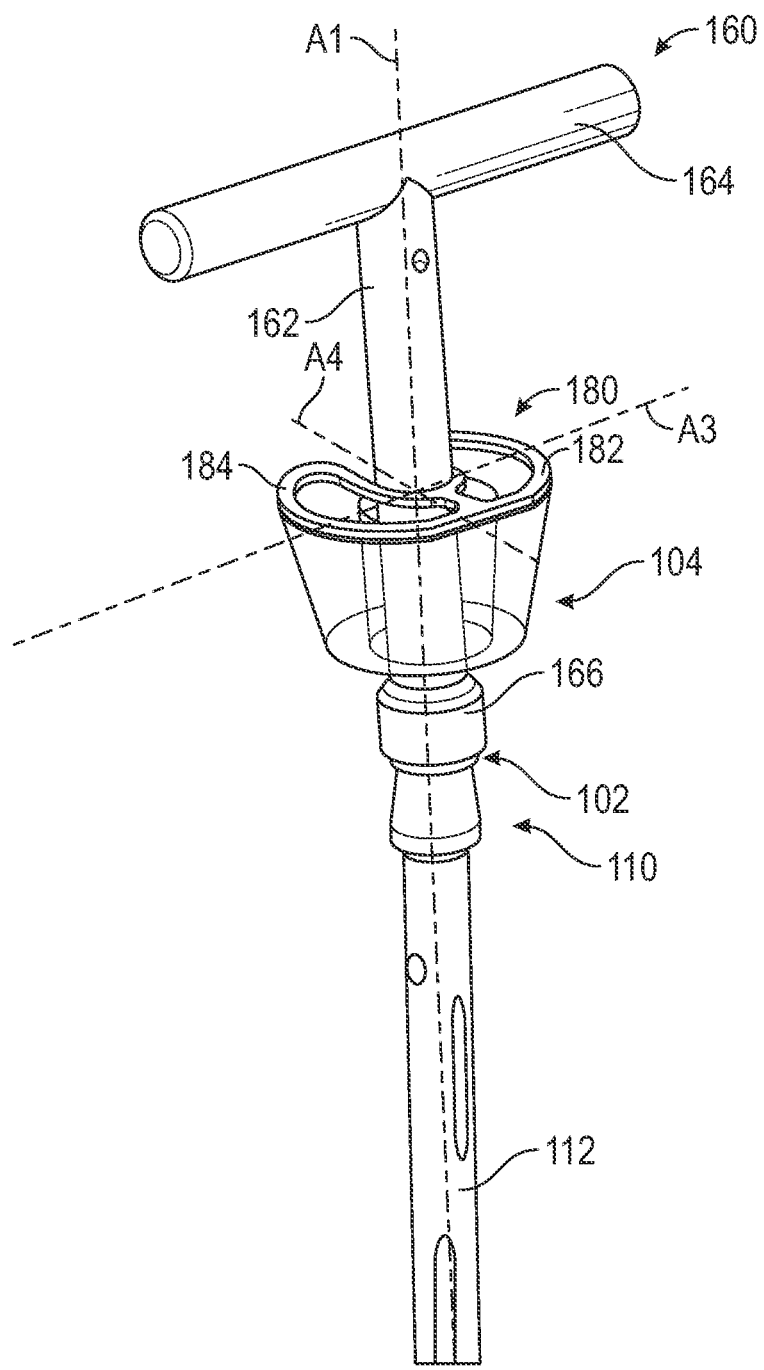
FIG. 10 is a perspective view of the insertion tool of FIG. 9A attached to a trial stem and an alignment guide that can provide depth guide and shape template functions.

FIG. 10 is a perspective view of insertion tool 160 of reaming system 100 of FIG. 9A having alignment guide 180 attached to insertion tool 160. Alignment guide 180 can comprise frame 182 that forms slot 184. Frame 182 can define an outer perimeter shape that approximates the shape of bone-removal envelope 104. Frame 182 can have an oblong shape with major axis A3 and minor axis A4. Frame 182 can provide a visual indication to a user of insertion tool 160 as to the orientation of articulating guide device 102, a minimum depth for a cone application or proper depth for a sleeve application. Frame 182 can have an outer perimeter that generally matches the shape of template 128 (FIG. 6).

In a first example, insertion tool 160 can be configured so that handle 164 extends along an axis that is parallel to face 130. Handle 164 can be configured to extend medial-laterally across the bone into which trial stem 110 is inserted. Face 130 can additionally extend parallel to straight back wall 131B of bone-removal template 128. As such, the user can know that straight back wall 131B of bone-removal template 128 and, hence, straight back wall 148B of bone-removal envelope 104 will be oriented medial-laterally. The user can adjust the position of handle 164 to any desirable orientation of straight back wall 131B, such as according to a surgical plan for implanting a prosthesis.

In a second example, alignment guide 180 can be attached to shaft 162 to provide a visual indication of the shape of bone-removal envelope 104. Alignment guide 180 can have a racetrack shape that mimics the travel path of the reamer. Alignment guide 180 can be positioned so that axis A3 is configured to extend medial-laterally across the bone into which trial stem 110 is inserted, and axis A4 is configured to extend anterior-posteriorly across the bone into which trial stem 110 is inserted. Axis A3 can extend parallel to straight back wall 131B of bone-removal template 128. As such, the user can know that straight back wall 131B of bone-removal template 128 and, hence, straight back wall 148B of bone-removal envelope 104 will be oriented medial-laterally. The user can adjust the position of handle 164 to any desirable orientation of straight back wall 131B, such as according to a surgical plan for implanting a prosthesis. Furthermore, the position of alignment guide 180 along shaft 162 can provide a visual indication of a minimum depth for a cone application or proper depth for a sleeve application. For example, alignment guide 180 can be positioned so that when reaming has been performed to a suitable depth, alignment guide 180 can be flush with a resected bone surface, such as resected surface 70 of FIG. 3.

Figure 11A:
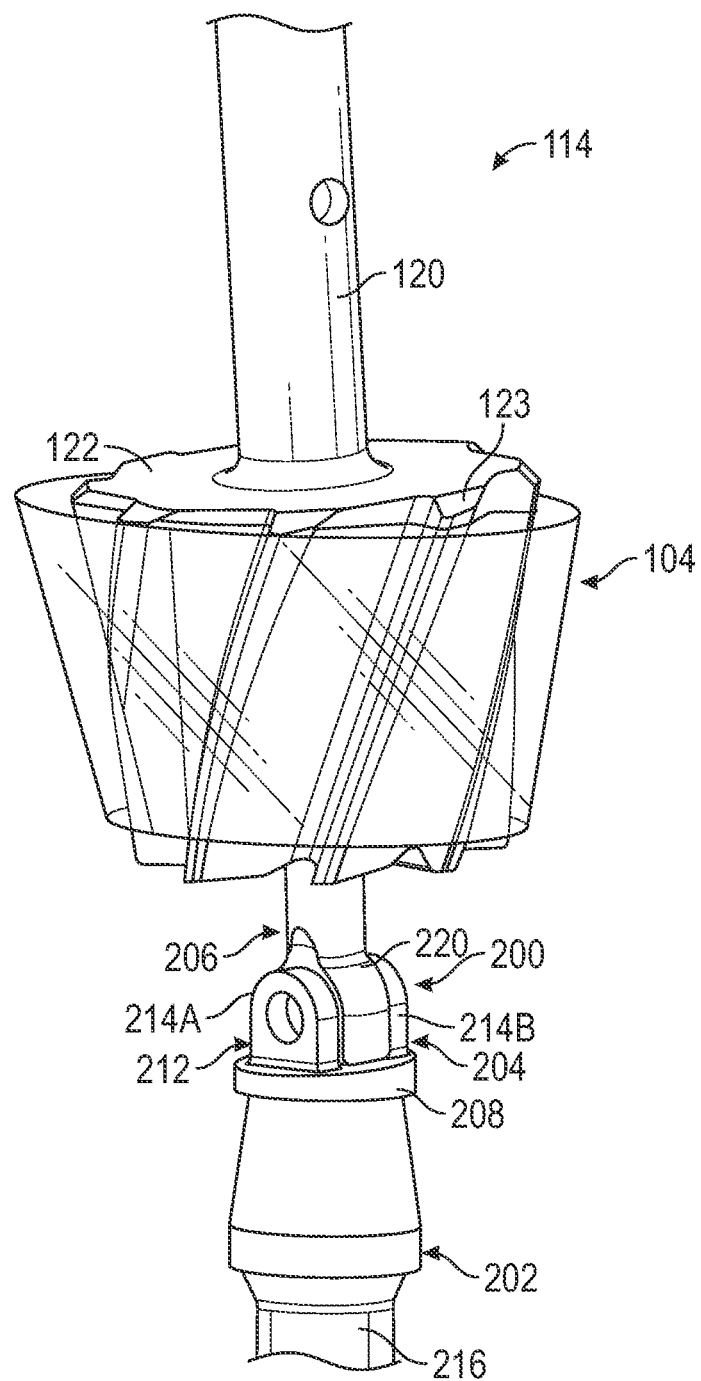
FIG. 11A is a perspective view of another example of a pivoting guidepost of the present disclosure connected to a trial stem cap via a pivot hinge comprising a pin.
Figure 11B:
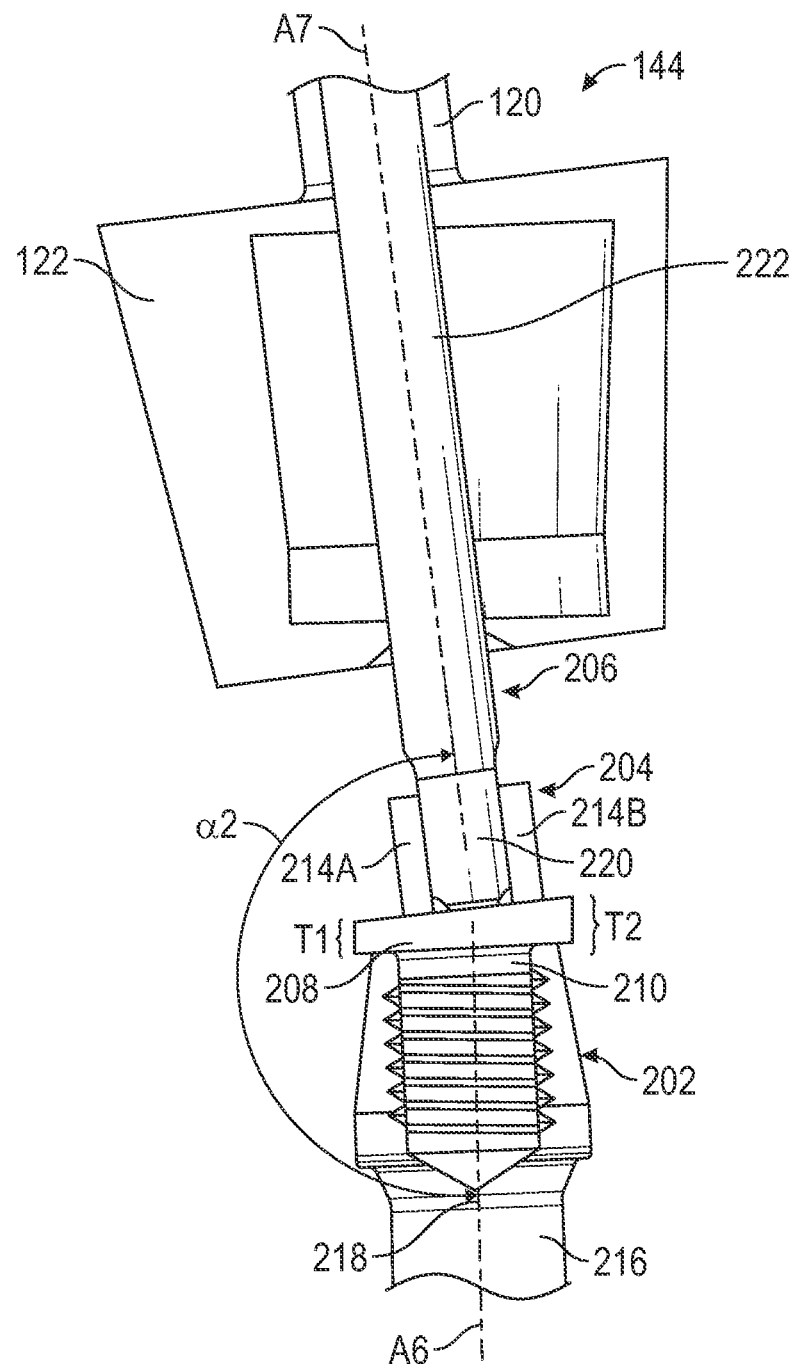
FIG. 11B is a side view of the pivoting guidepost of FIG. 11A illustrating angling of the guidepost relative to the cap with an angled alignment to the stem provisional axis.
Figure 11C:
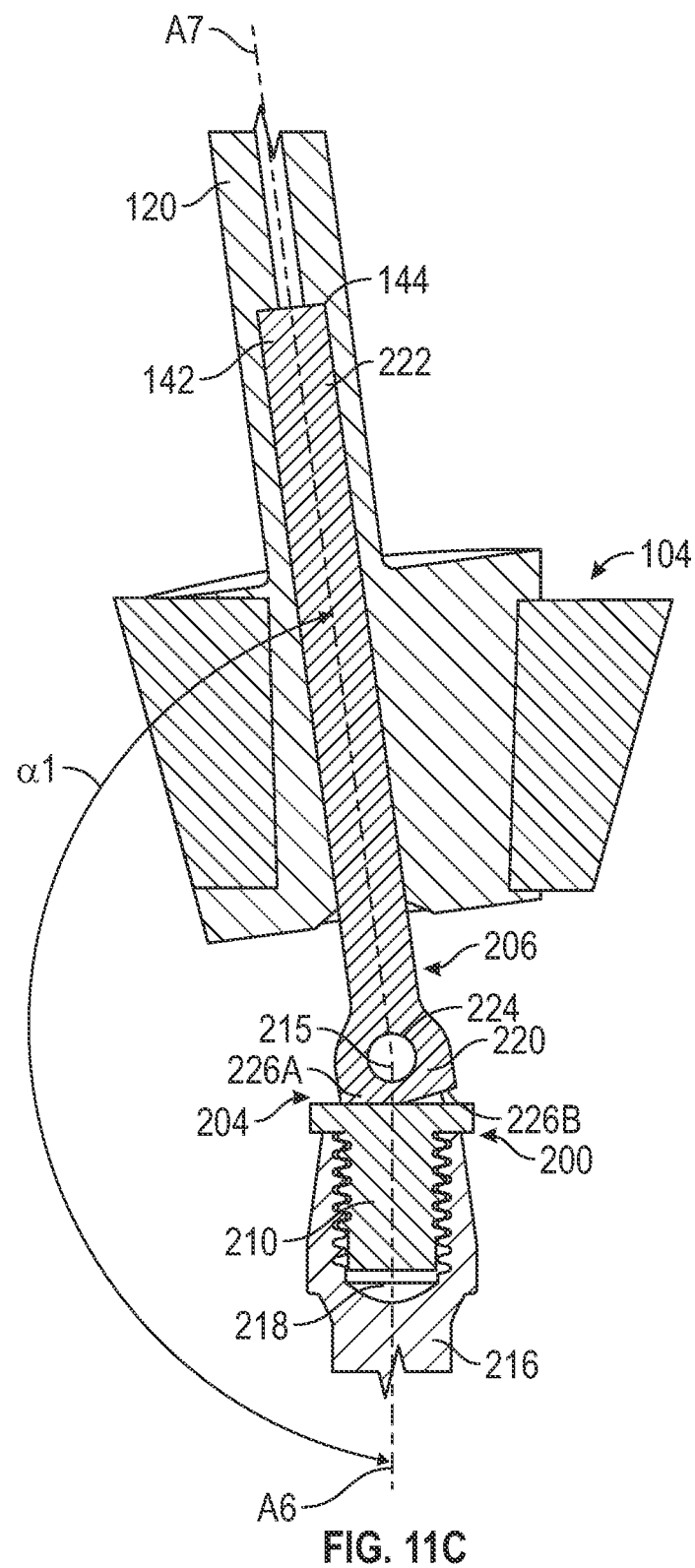
FIG. 11C is a side cross-sectional view of the pivoting guidepost of FIG. 11A showing stop features for the guidepost.

FIG. 11A is a perspective view of pivoting guide device 200 of the present disclosure connected to trial stem 202. Pivoting guide device 200 can be used with cannulated reamer 114. Pivoting guide device 200 can comprise cap 204 and guidepost 206. FIG. 11B is a side view of pivoting guide device 200 of FIG. 11A illustrating angling of guidepost 206 relative to cap 204. FIG. 11C is a side cross-sectional view of pivoting guide device 200 of FIG. 11A showing stop surfaces 226A and 226B of guidepost 206. Cap 204 can comprise base 208, stem 210 and bracket 212. Bracket 212 can comprise flanges 214A and 214B, which can each have a bore for receiving pivot pin 215 (FIG. 11C). Stem 210 can comprise a threaded body configured for coupling to trial stem 202. Trial stem 202 can comprise elongate body 216 and socket 218. Guidepost 206 can comprise eyelet 220 and stem 222. Eyelet 220 can comprise bore 224, first stop surface 226A and second stop surface 226B. Trial stem 202 can be inserted into bone along axis A6. Stem 222 can extend from bracket 212 along axis A7. FIGS. 11A-11C are discussed concurrently.

As can be seen in FIG. 11C, pivoting guide device 200 can move cannulated reamer 114 within a plane encompassing stem 222 such that angle α1 is variable. In particular, pivoting guide device 200 can sweep cannulated reamer 114 along a single plane determined by the hinge formed at pin 215 extended through flange 214A, flange 214B and eyelet 220. Flanges 214A and 214B can prevent rotation of stem 222 about axis A6 such that stem 222 is restricted to pivoting in a single plane. The amount of angulation of stem 222 relative to cap 204 can be controlled by stop surfaces 226A and 226B on the bottom or distal surface of eyelet 220. The greater amount that stop surfaces 226A and 226B are angled inward toward stem 222, the more amount of articulation of stem 222 is permitted. Thus, stem 222 can be coaxial with trial stem 202 and can be articulated at pin 215 to allow angle α1 to be increased or decreased amounts controlled by stop surfaces 226A and 226B. In examples, stop surfaces 226A and 226B can be symmetric such that angle α1 can be varied equally in both directions relative to vertical. In other examples, stop surfaces 226A and 226B can be asymmetric or complex such that angle α1 can be varied disproportionately on either side of vertical.

As can be seen in FIG. 11B, stem 222 can be angled relative to trial stem 202 such that angle α2 is between axis A6 and axis A7, i.e., axes A6 and A7 are non-parallel. Angle α2 between stem 222 and trial stem 202 can be controlled by the thickness of base 208. Base 208 can comprise a disk having a flat bottom surface and a flat top surface. The top surface can be closer to the bottom surface on one side of base 208 to form thickness T1 and the top surface can be further away from the bottom surface on an opposite side of base 208 to form thickness T2, wherein T2 is greater than T1. As such, base 208 can be wedge shaped. In additional examples, axes A6 and A7 can be parallel.

In examples, pivoting guide device 200 can be configured such that angle α1 can be varied in a medial-lateral or coronal plane of the anatomy and angle α2 can lie in an anterior-posterior or sagittal plane. However, pivoting guide device 200 can be configured to have other orientations for angle α1 and angle α2. In the illustrated example, cap 204 is configured such that stem 222 extends from the center of base 208. However, cap 204 can be configured such that stem 222 is offset from the center of base 208.

Figure 12A:
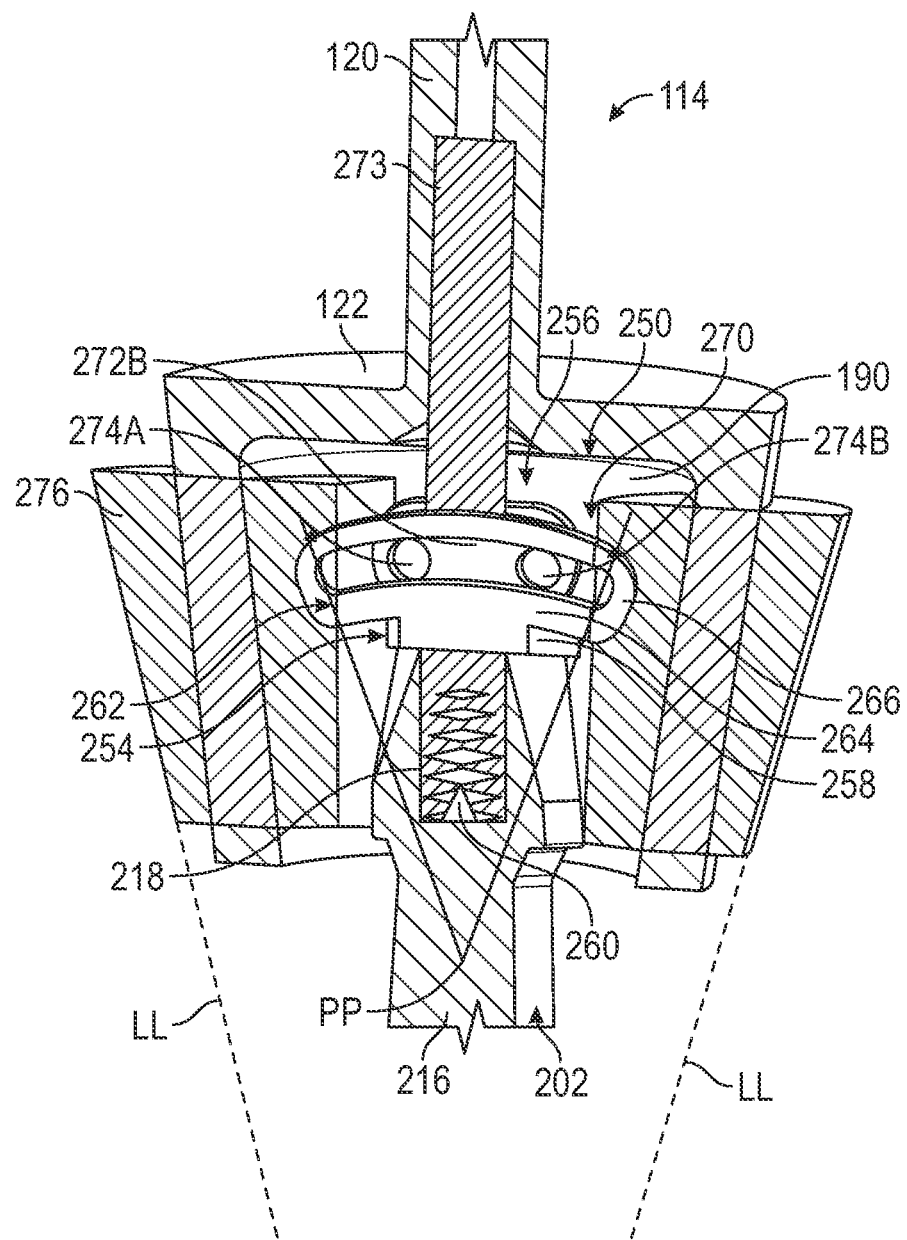
FIG. 12A is a perspective view of another example of a pivoting guidepost of the present disclosure connected to a trial stem cap via a pivot hinge comprising a slide track.
Figure 12B:
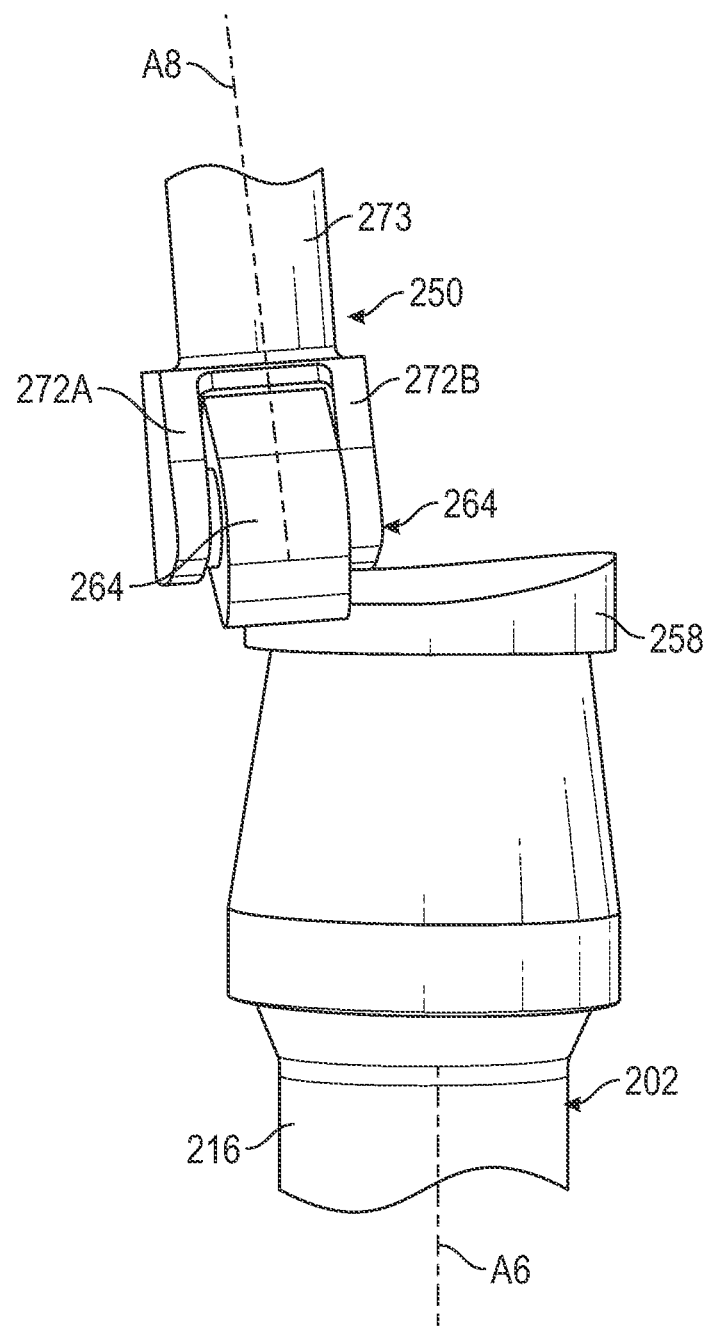
FIG. 12B is a side view of the slide track of FIG. 12A illustrating offset and angling of the slide track relative to an axis of a trial stem.

FIG. 12A is a perspective view of pivoting guide device 250 of the present disclosure connected to trial stem 202. Pivoting guide device 250 can be used with cannulated reamer 114. Cannulated reamer 114 can comprise socket 190 within cutter 122 to allow pivoting guide device 250 to be recessed within cutter 122 to allow cutter 122 to be brought closer to pivot point PP. Pivoting guide device 250 can comprise cap 254 and guidepost 256. Cap 254 can comprise base 258, stem 260 and bracket 262. Bracket 262 can comprise rail 264, which can have slot 266 for receiving a slide body or a pair of pivot pins. Stem 260 can comprise a threaded body configured for coupling to trial stem 202. Trial stem 202 can comprise elongate body 216 and socket 218. Guidepost 256 can comprise shuttle 270, which can comprise flanges 272A and 272B (FIG. 12B), and guidepost 273. Flanges 272A and 272B can comprise bores 274A and 274B for receiving slide pins (not shown). FIG. 12B is a side view of shuttle 270 of FIG. 12A offset of guidepost 273 relative to elongate body 216. FIGS. 12A and 12B are discussed concurrently.

In the example of FIGS. 12A and 12B, the effective pivot point of guidepost 273 can be lower relative to the examples of FIGS. 5-8 and 11A-11C. For example, the effective pivot point of the example of FIGS. 5-8 is where ball 126 is located directly between stem 124 and trial stem 110. Likewise, in the example of FIGS. 11A-11C, the effective pivot point is at pin 215. However, in the example of FIGS. 12A and 12B, the effective pivot point PP is located at the center of the curve for arcuate slot 266. It can be desirable to have pivot point PP further down along the length of elongate body 216 to be closer to where lines LL extending inwardly of the sides of bone-removal envelope 276 would converge to, for example, allow the shape of cutter 122 to closer match the shape of bone-removal envelope 276 without articulation of cannulated reamer 114, but without having to extend pivoting guide device 250 deep down into the bone.

Furthermore, as can be seen in FIG. 12B, axis A8 of guidepost 273 can be offset and angled relative to axis A6 of elongate body 216. Base 258 can be constructed to have varying thickness similar to base 208 of FIG. 11B. As discussed herein, offsetting of axis A6 and axis A8 relative to a horizontal plane an angling of axis A8 relative to axis A6 can be factors in producing complex shaped bone pockets for receiving sleeves and cones, along with the depth of pivot point PP, the angulation provided by bracket 262 and shuttle 270 in a single plane, the articulation of articulating guide device 102 of FIGS. 5-8 in multiple planes, and the shape of cutter 122 (which can be cylindrical or conical with different wall angles). In additional examples, guidepost 273 can be aligned or parallel to axis A6.

Figure 13A:
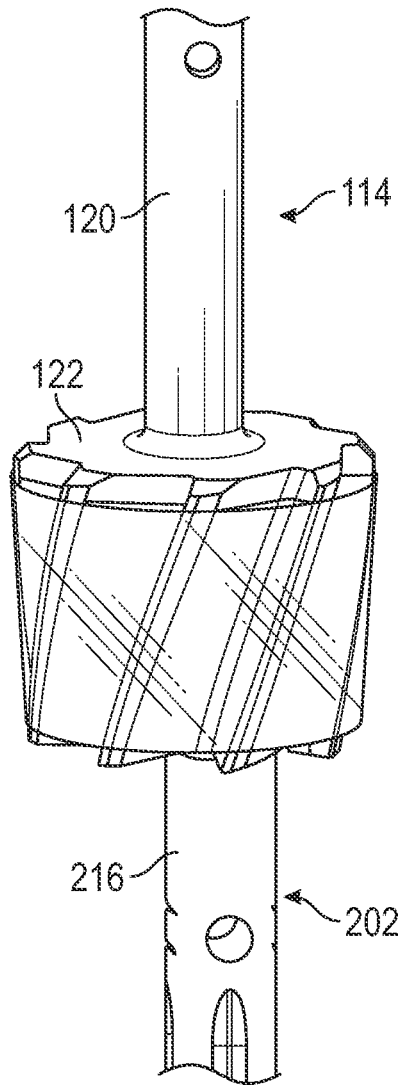
FIG. 13A is a perspective view of an offset and fixed guidepost connected to a reamer to produce an offset sleeve pocket.
Figure 13B:
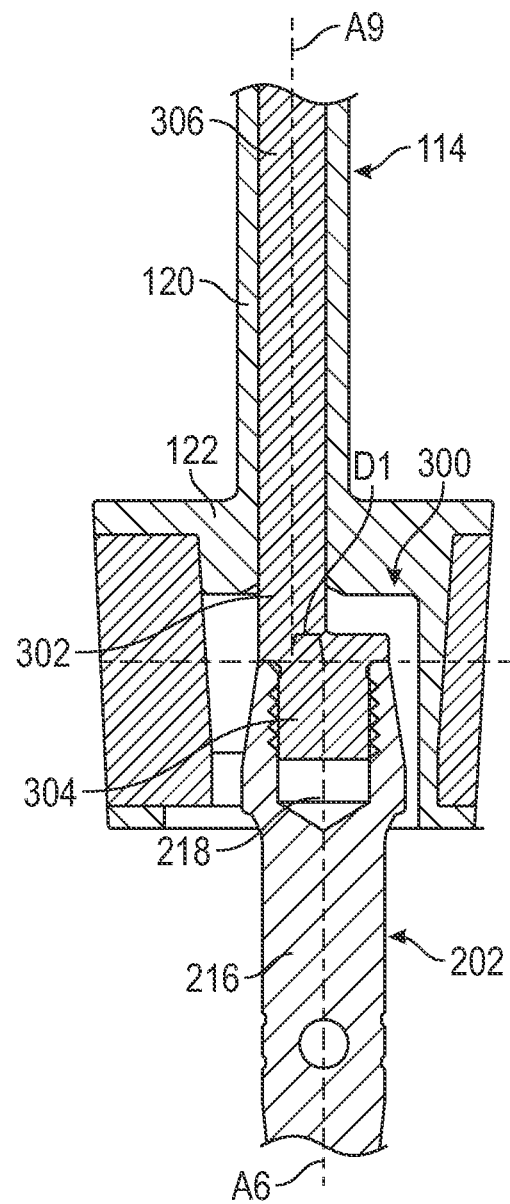
FIG. 13B is a cross-sectional view of the fixed guidepost of FIG. 13A showing the guidepost parallel to and offset from the trial stem.

FIG. 13A is a perspective view of fixed guide device 300 of the present disclosure connected to trial stem 202. Fixed guide device 300 can be used with cannulated reamer 114. Fixed guide device 300 can comprise base 302, coupler 304 and guidepost 306. FIG. 13B is a cross-sectional view of fixed guide device 300 of FIG. 13A showing guidepost 306 extending along axis A9 parallel to and offset from axis A6 of trial stem 202 distance D1. FIGS. 13A And 13B are discussed concurrently.

Figure 14A:
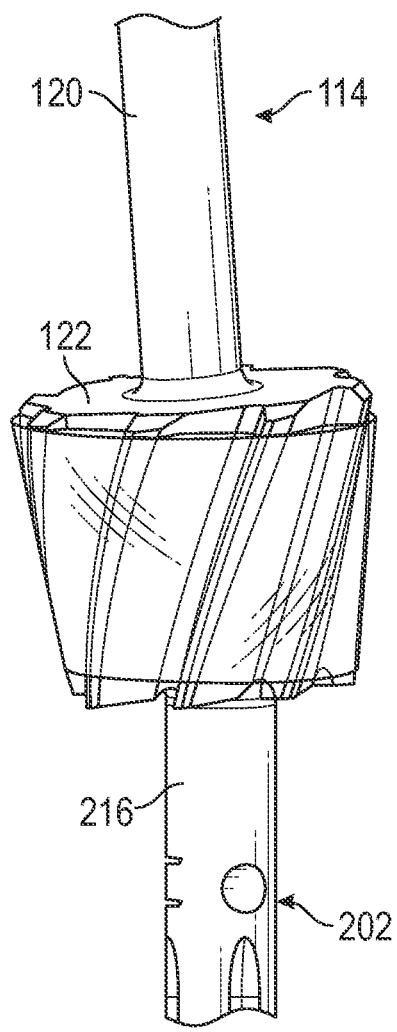
FIG. 14A is a perspective view of a fixed guidepost connected to a reamer to produce a non-aligned or oblique sleeve pocket.
Figure 14B:
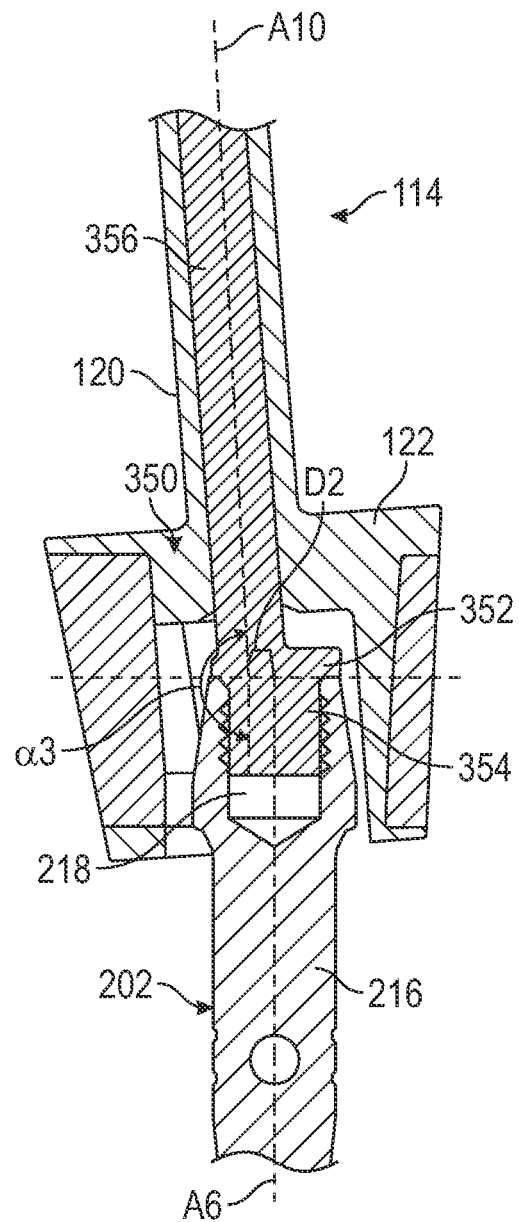
FIG. 14B is a cross-sectional view of the fixed guidepost of FIG. 14A showing the guidepost oblique to and offset from the trial stem.

FIG. 14A is a perspective view of a fixed guide device 350 of the present disclosure connected to trial stem 202. Fixed guide device 350 can be used with cannulated reamer 114. Fixed guide device 350 can comprise base 352, coupler 354 and guidepost 356. FIG. 13B is a cross-sectional view of fixed guide device 350 of FIG. 14A showing guidepost 356 extending along axis A10 angled to axis A6 at angle 3 and offset from axis A6 of trial stem 202 distance D2. FIGS. 14A and 14GB are discussed concurrently.

FIGS. 13A-14B illustrate examples of fixed guide devices without pivoting or articulation. Thus, distances D1 and D2 and angle α3 can be fixed. The devices of FIGS. 13A-14B can comprise simpler, e.g., non-pivoting, devices than those of FIGS. 5-12B, but that still can form offset, angled, partially-symmetric or asymmetric bone pockets.

Figure 15:
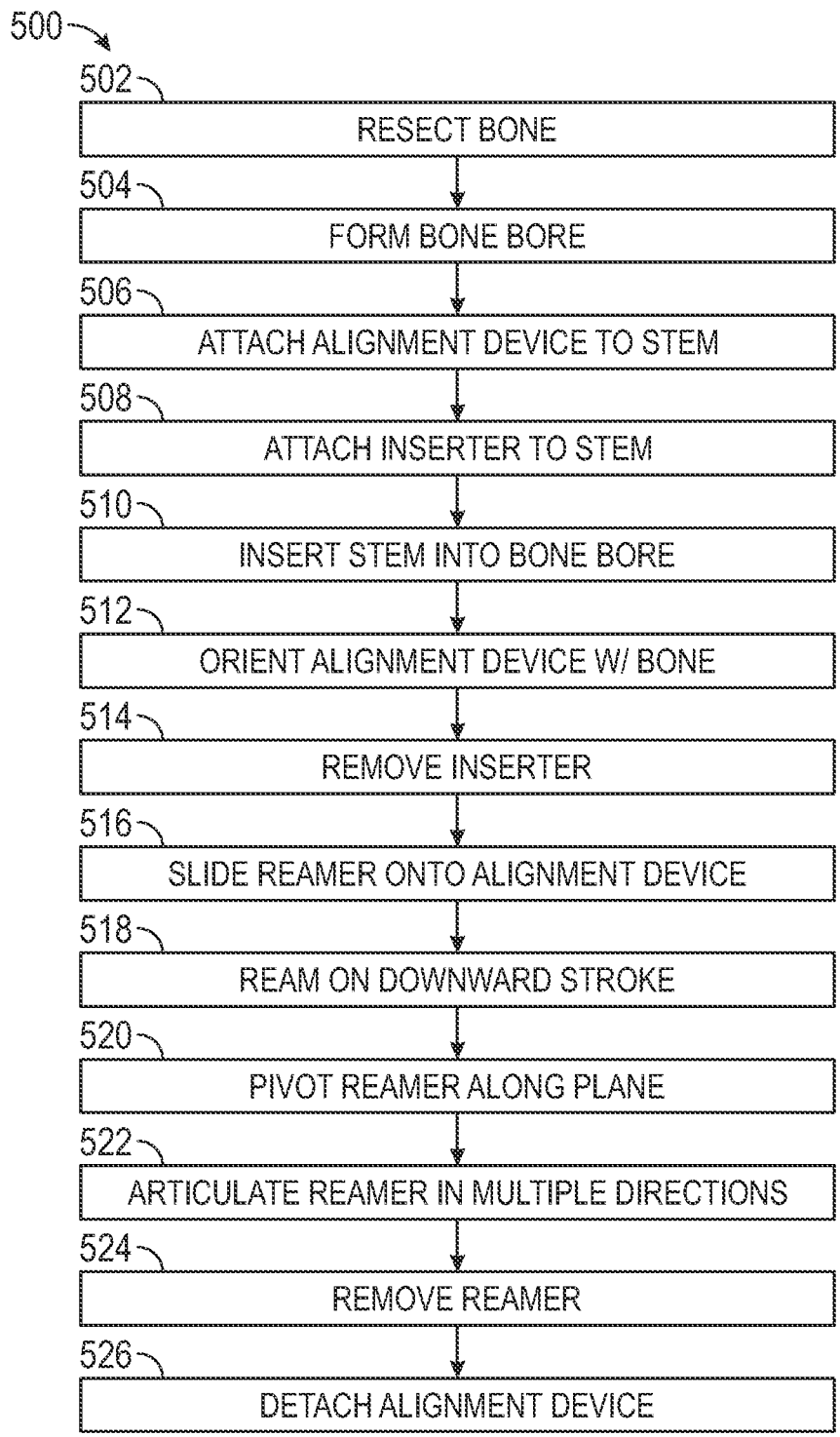
FIG. 15 is a line diagram illustrating steps of methods for reaming a long bone to receive a complex shaped, offset or non-aligned sleeve or cone.

FIG. 15 is a line diagram illustrating steps of method 500 for reaming or otherwise forming offset, angled, variable, non-aligned, partially-symmetric and asymmetric bone pockets using the instrumentation described in the present disclosure.

At operation 502, a bone can be prepared to receive a stem of a prosthetic device. For example, a long bone, such as a tibia of a femur can be resected to expose an intramedullary canal. Tibia T of FIG. 4 can be modified to produce resected surface 70.

At operation 504, a bone bore can be formed in the bone of operation 502. For example, the intramedullary canal can be broached or reamed to form an elongate passage to receive the stem of the prosthetic device. Tibia T of FIG. 4 can be modified to produce stem channel 54.

At operation 506, a reaming alignment device of the present disclosure can be attached to a stem. In examples, the stem can be a stem provisional. For example, device 102 of FIG. 5, device 200 of FIG. 11A, device 250 of FIG. 12A, device 300 of FIG. 13B and device 350 of FIG. 14B can be attached to trial stem 110 or trial stem 202.

At operation 508, an inserter can be attached to the stem. For example, the inserter can be positioned over the reaming alignment device of operation 506. Insertion tool 160 of FIGS. 9A-9C can used. Additionally, alignment guide 180 can be attached to insertion tool 160 at this point of the procedure.

At operation 510, the stem can be inserted into the bone bore formed at operation 504. Trial stem 110 or trial stem 202 can be pushed into the bone bore with or without insertion tool 160. Likewise, an alignment device, such as alignment guide 180, can be inserted into the bone bore.

At operation 512, the alignment device can be oriented relative to the anatomy of the bone to additionally align the stem attached to the inserter. For example, the inserted can be rotated to orient. Handle 164 of insertion tool 160 can be aligned with the medial-lateral direction. Alignment guide 180 can also be oriented to match the shape of frame 182 with anatomy, e.g., to position frame 182 over resected surface 70 in the desired location for the bone removal envelope, e.g., bone-removal envelope 104 of FIG. 5.

At operation 514, the inserter can be removed, such as by being detached from the stem. Insertion tool 160 can be uncoupled from trial stem 110 or trial stem 202.

At operation 516, a reaming tool can be attached to the reaming alignment device of operation 506. Cannulated reamer 114 can slid over stem 124, stem 222, guidepost 273, guidepost 306 or guidepost 356 via insertion into channel 142.

At operation 518, the reaming tool can be operated to ream axially along the reaming alignment device. Cannulated reamer 114 can be moved distally along one of stem 124, stem 222, guidepost 273, guidepost 306 or guidepost 356 to remove bone.

At operation 520, the reaming alignment device can be pivoted using the reaming tool to perform reaming along a vertical plane. The reaming tool can be pivoted along a plane or within a bone removal template as described herein. For example, cannulated reamer 114 can be pivoted using device 102 of FIG. 5, device 200 of FIG. 11A or device 250 of FIG. 12A.

At operation 522, the reaming alignment device can be articulated using the reaming tool in multiple directions to perform reaming within a horizontal plane. For example, cannulated reamer 114 can be articulated using device 102 of FIG. 5.

At operation 524, the reaming tool can be removed from the reaming alignment device. Cannulated reamer 114 can be withdrawn from stem 124, stem 222, guidepost 273, guidepost 306 or guidepost 356.

At operation 526, the reaming alignment device can be removed from the stem. For example, device 102 of FIG. 5, device 200 of FIG. 11A, device 250 of FIG. 12A, device 300 of FIG. 13B and device 350 of FIG. 14B can be removed from trial stem 110 or trial stem 202.

As such, a cone or sleeve can be temporarily positioned around the stem to evaluate the reaming of operations 518-522. If the cone or sleeve fits the produced bone pocket produced by operations 502-526, the trial stem can be removed and the cone or sleeve and a stem can be assembled and inserted into the bone for implantation. If the cone or sleeve is found to not adequately match or mate with the reamed bone pocket, additional reaming can be performed if desired before the final prosthetic construct is positioned for implantation.

FIGS. 16A-19C show an example of articulating guide device 600 having a spherical racetrack reamer guide, wherein a guidepost is configured to spherically pivot relative to a trial stem via an effective pivot point that is projected downward along the trial stem. Articulating guide device 600 can be configured to produce bone pockets or envelopes (e.g., spaces within bone), or sleeve sockets, that can accept uniformly shaped, partially-symmetric, asymmetric and complex shaped sleeves or cones.

Figure 16B:
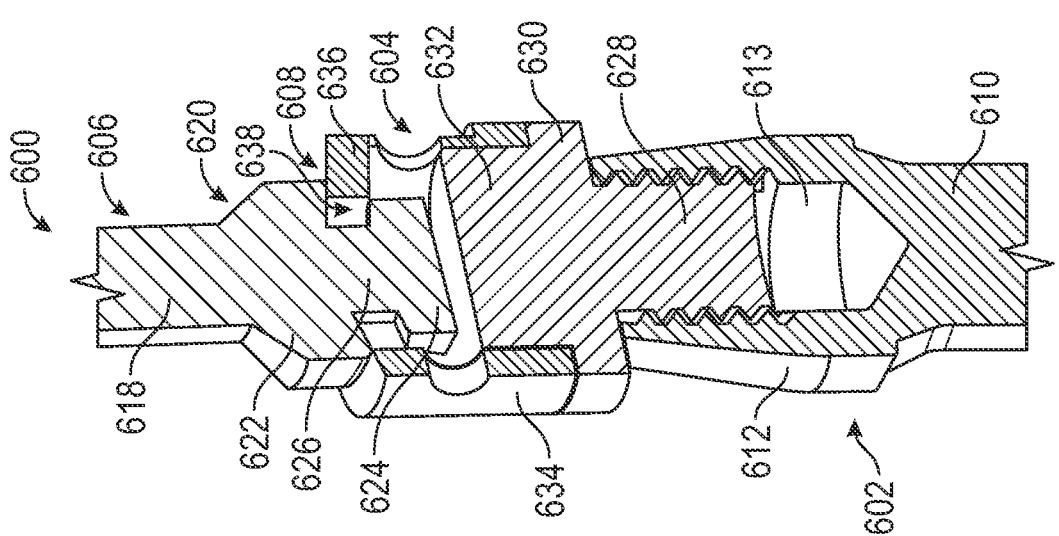
FIG. 16B is a cross-sectional view of the articulating guide device of FIG. 16A showing a spherical racetrack interface between a reamer guidepost and the cap.
Figure 16A:
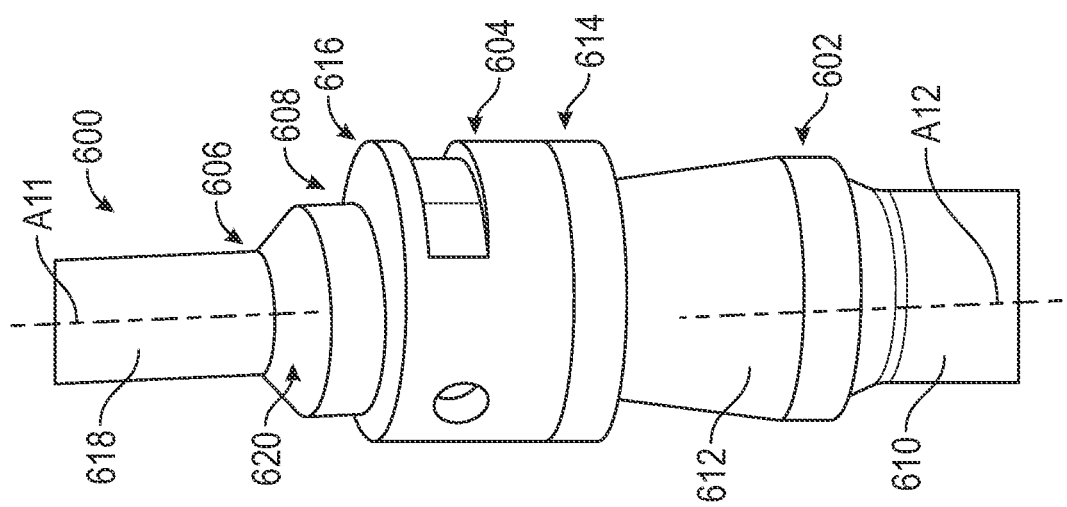
FIG. 16A is a perspective view of an articulating guide device coupled to a trial stem via a cap including a spherical racetrack interface.

FIG. 16A is a perspective view of articulating guide device 600 coupled to trial stem 602. FIG. 16B is a cross-sectional view of articulating guide device 600 of FIG. 16A. FIGS. 16A and 16B are discussed concurrently. Articulating guide device 600 can comprise cap 604 and reamer guidepost 606. Reamer guidepost 606 and cap 604 can be connected by spherical racetrack interface 608. Trial stem 602 can be constructed similarly as trial stem 202 described herein and can include elongate body 610 and head 612, which can include socket 613 (FIG. 16B). Elongate body 610 can extend along axis A11.

Cap 604 can comprise coupler 614 and limiter 616. Reamer guidepost 606 can comprise stem 618 and spherical limiter 620. Spherical limiter 620 can comprise spherical ledge 622, spherical knob 624 and post 626. Spherical socket 627 can be formed between spherical ledge 622 and spherical knob 624. Coupler 614 can comprise shaft 628, base 630 and head 632. Limiter 616 can comprise wall 634, spherical plate 636 and template 638.

Shaft 628 of coupler 614 can be attached to socket 613 of trial stem 602, such as by threaded engagement or interference fit. Wall 634 of limiter 616 can be attached to head 632 of coupler 614. Spherical knob 624 of reamer guidepost 606 can be positioned within wall 634 such that spherical plate 636 of limiter 616 is positioned within spherical socket 627, thereby positioning spherical ledge 622 against spherical plate 636. In examples, limiter 616 can be formed of two separate pieces that are coupled together around spherical knob 624. In additional examples, limiter 616 and reamer guidepost 606 can be simultaneously manufactured using additive manufacturing processes. In examples, spherical knob 624 can be separately attached to post 626 via a fastener or other coupling means.

Spherical limiter 620 can permit guidepost 606 to multi-directionally articulate to allow cannulated reamer 650 (FIG. 19A) to change orientation relative to trial stem 602 such that axis A11 can change angles relative to axis A12. In particular, spherical plate 636 can engage with spherical knob 624 to allow reamer guidepost 606 to move within a spherical-shaped envelope or semi-spherical shaped envelope. Specifically, the envelope can comprise a portion of a sphere defined by the shape of template 638.

Figure 17:
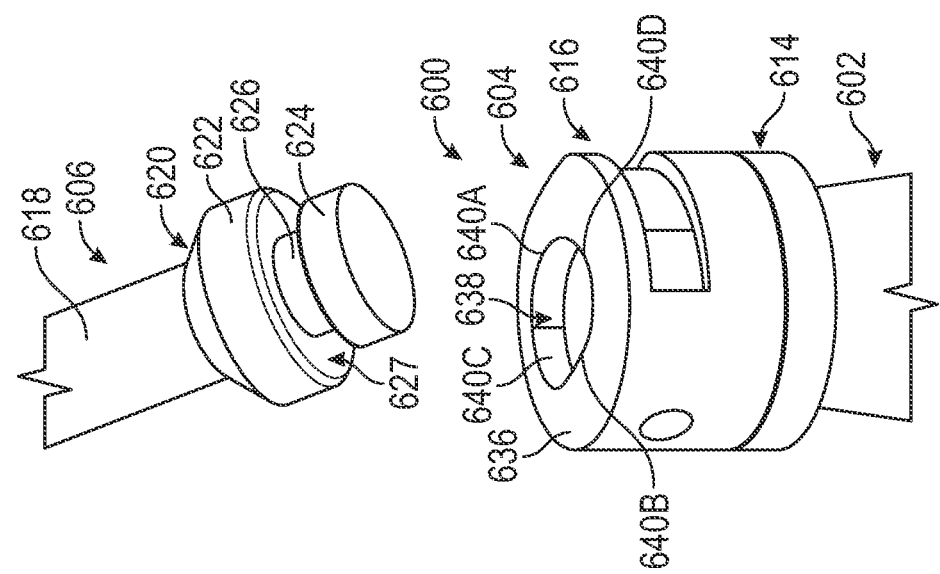
FIG. 17 is an exploded view of the articulating guide device of FIG. 16A showing the reamer guidepost and the cap.

FIG. 17 is a perspective view of articulating guide device 600 of FIG. 16A with reamer guidepost 606 removed. Cap 604 can be attached to trial stem 602. In particular, coupler 614 can be attached to trial stem 602 and limiter 616 can be attached to coupler 614. Limiter 616 can include spherical plate 636 in which template 638 is located.

Template 638 can comprise a bone-removal template that comprises a shape to which a cross-section of a bone pocket is made to receive a sleeve or cone. In the illustrated example, template 638 can have curved front wall 640A, straight back wall 640B, curved side wall 640C and curved side wall 640D. Curved front wall 640A can be configured to face in the anterior direction and extend proximate a cortical bone wall at an anterior of a tibial plateau and straight back wall 640B can be configured to face in the posterior direction and extend proximate a cortical bone wall at a posterior of a tibial plateau. Walls 640A-640D can form a D-shaped oval. However, template 638 can have other shapes. Walls 640A-640D can limit movement of stem 618, and therefore cannulated reamer 650 (FIGS. 19A-19C), so that cannulated reamer 650 can produce a bone-removal envelope.

Spherical socket 627 can receive spherical plate 636 to allow post 626 to move within template 638. In particular, an upper surface of spherical plate 636 can engage with a lower surface of spherical ledge 622 and a lower surface of spherical plate 636 can engage with an upper surface of spherical knob 624. However, spherical socket 627 can be taller than spherical knob 624 such that all surfaces need not be touching and to facilitate articulation of reamer guidepost 606. The spherical surfaces can have the same center point to allow reamer guidepost 606 to move in a spherical pattern, as shown in FIG. 18.

FIG. 18 is a cross-sectional view of articulating guide device 600 of FIGS. 16A-17 showing spherical guide path 644 and effective pivot point 646. Spherical guide path 644 can comprise a surface revolved around axis A11 having curvature that matches the curvature of spherical ledge 622, spherical plate 636 and spherical knob 624. Due to the spherical curvature of spherical ledge 622, spherical plate 636 and spherical knob 624, the center of movement for reamer guidepost 606 can be located at effective pivot point 646 below spherical racetrack interface 608.

Figure 19C:
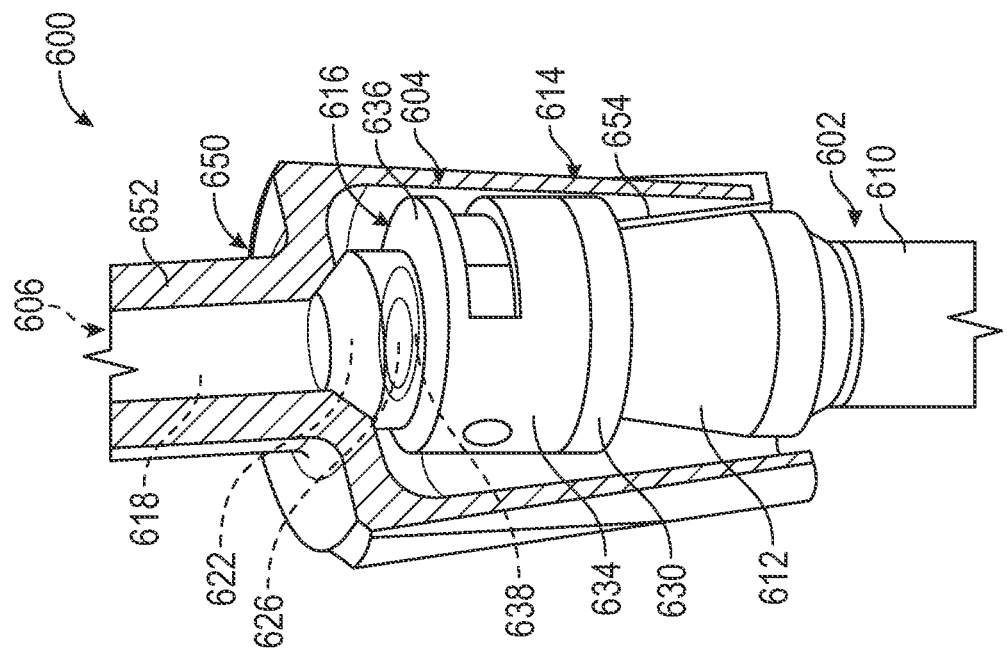
FIG. 19C is a cross-sectional view of the reamer with the guidepost shown in phantom to show the spherical racetrack interface.
Figure 19B:
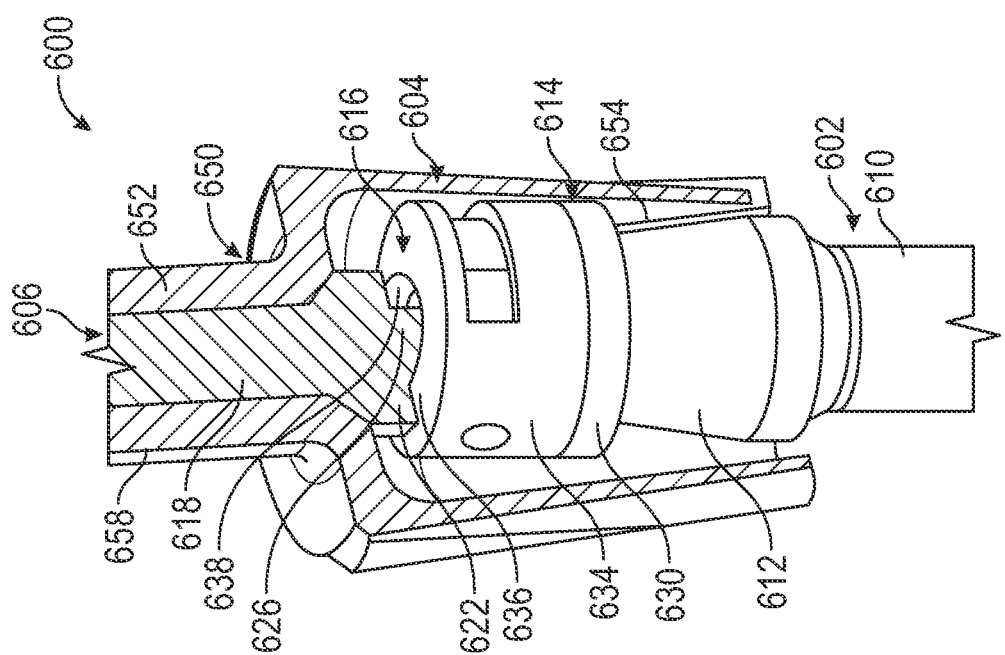
FIG. 19B is a cross-sectional view of the reamer and articulating guide device of FIG. 18 with the cap shown in full to illustrate the spherical racetrack interface.

In the example of FIGS. 16A-18, effective pivot point 646 of reamer guidepost 606 can be lower relative to the examples of FIGS. 5-8 and 11A-11C. For example, the effective pivot point of the example of FIGS. 5-8 is where ball 126 is located directly between stem 124 and trial stem 110. Likewise, in the example of FIGS. 11A-11C, the effective pivot point is at pin 215. However, in the example of FIGS. 16A-18, effective pivot point 646 can be located at the center of curvature of spherical ledge 622, spherical plate 636 and spherical knob 624. It can be desirable to have effective pivot point 646 further down along the length of elongate body 610 to more closely match the shape of cannulated reamer 650, as shown in FIGS. 19A-19C. As such, angled reaming can be performed further down within tibia T (FIG. 2) to more closely match the angles of cortical bone within tibia T and without compromising the integrity of tibia T, e.g., without coming close to the exterior of cortical bone.

FIG. 19A is a cross-sectional view of cannulated reamer 650 positioned around reamer guidepost 606 of articulating guide device 600 of FIG. 16A. FIG. 19B is a cross-sectional view of cannulated reamer 650 and articulating guide device 600 of FIG. 19B with cap 604 shown in full to illustrate spherical racetrack interface 608. FIG. 19C is a cross-sectional view of cannulated reamer 650 with reamer guidepost 606 shown in phantom to show spherical racetrack interface 608. FIGS. 19A-19C are discussed concurrently.

Cannulated reamer 650 can be constructed similarly to other reamers described herein, such as cannulated reamer 114. Cannulated reamer 650 can slide along reamer guidepost 606. Cannulated reamer 650 can comprise cannulated shaft 652 and cannulated cutter 654, which can include teeth 656. Cannulation 658 can extend through cannulated cutter 654 and into cannulated shaft 652. Cannulation 658 can include receptacle portion 660 that can fit over cap 604 and head 612 of trial stem 602. Walls of cannulated cutter 654 can extend along lines L3 to form a trapezoidal bone-removal envelope. In examples, lines L3 can be configured to converge at or near effective pivot point 646. In additional examples, lines L3 can be configured to converge distal, e.g., further into the bone, of effective pivot point 646. As such, the curvatures of spherical ledge 622, spherical plate 636 and spherical knob 624 can be based on the angle between lines L3. Thus, the shape of cannulated cutter 654 can more closely match the shape of a cone or sleeve without having to extend spherical racetrack interface 608 deep down into the bone.

As can be seen in FIGS. 19B and 19C, post 626 can be configured to engage walls 640A-640D of template 638. Post 626 can have a cylindrical profile and walls 640A-640D can be planar. The surfaces of post 626 and walls 640A-640D can be arranged parallel to axis A11. However, in other examples, the surfaces of post 626 and walls 640A-640D can be angled to conform with the angle between axis A12 and walls 640A-640D. As can be seen in FIGS. 19B and 19C, the cross-sectional area of post 626 can be smaller than the cross-sectional area of template 638, thereby allowing reamer guidepost 606 to move between walls 640A-640D. The surface of post 626 can be curved relative to axis A11 to allow reamer guidepost 606 to move smoothly along walls 640A-640D.

In the illustrated example, cap 604 is configured to position axis A11 of reamer guidepost 606 co-axial with axis A12 of trial stem 602. However, in other configurations, cap 604 can position axis A11 offset from axis A12.

FIGS. 20A-23 show an example of articulating guide device 700 having an arcuate slide pad reamer guide, wherein a guidepost is configured to arcuately pivot relative to a trial stem via an effective pivot point that is projected downward along the trial stem. Articulating guide device 700 can be configured to produce bone pockets or envelopes (e.g., spaces within bone), or sleeve sockets, that can accept uniformly shaped, partially-symmetric, asymmetric and complex shaped sleeves or cones.

Figure 20B:
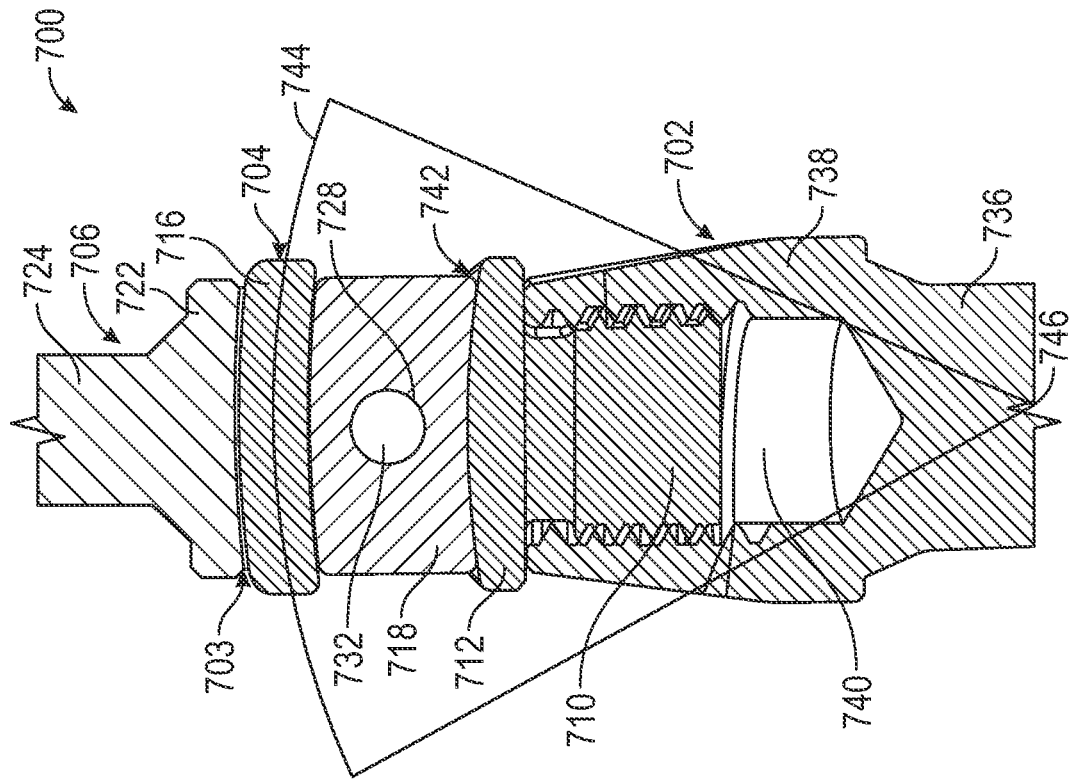
FIG. 20B is a cross-sectional view of the articulating guide device of FIG. 22 showing an arcuate plate of the retainer positioned between an arcuate ledge and an arcuate knob of the coupler.
Figure 20A:
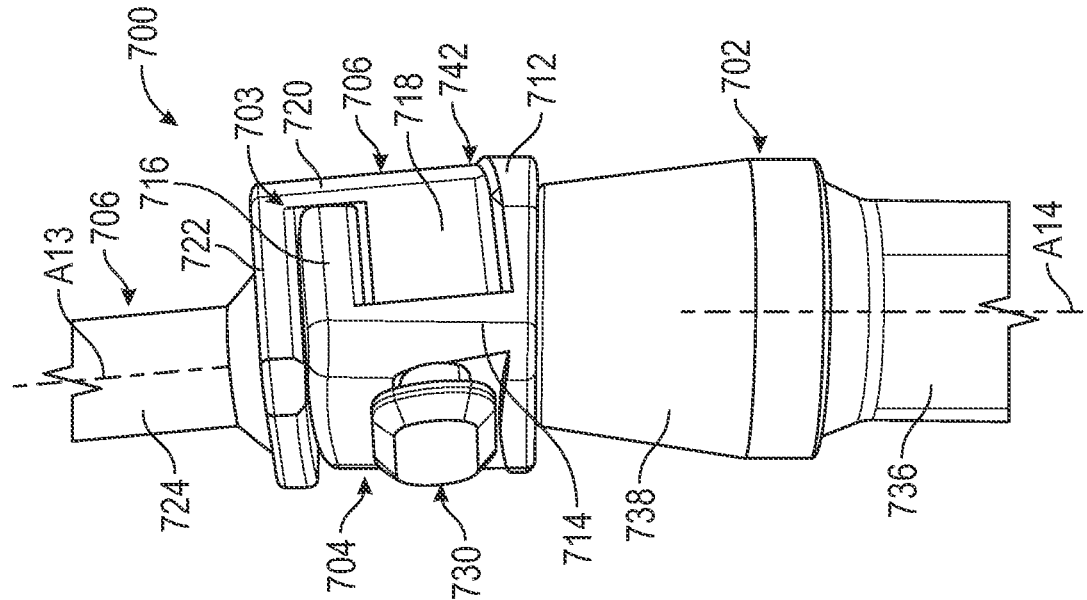
FIG. 20A is a perspective view of an articulating guide device coupled to a trail stem via a cap including an arcuate slide pad interface.

FIG. 20A is a perspective view of articulating guide device 700 coupled to trial stem 702 via arcuate slide pad interface 703. FIG. 20B is a cross-sectional view of articulating guide device 700 of FIG. 20A. FIGS. 20A and 20B are discussed concurrently. Articulating guide device 700 can comprise cap 704 and guide stem 706. Cap 704 can comprise shaft 710, arcuate base 712, sidewall 714 and arcuate plate 716.

Guide stem 706 can comprise arcuate knob 718, sidewall 720, arcuate ledge 722 and guidepost 724. Sidewall 714 of cap 704 can comprise arcuate slot 726 and sidewall 720 of guide stem 706 can include bore 728. Pin 730 can be inserted into arcuate slot 726 and bore 728. Pin 730 can comprise shaft 732 and head 734. Trial stem 702 can be constructed similarly as trial stem 202 described herein and can include elongate body 736 and head 738, which can include socket 740. Elongate body 736 can extend along axis A14. Arcuate slide pad interface 703 can comprise arcuate guide path 744 and effective pivot point 746.

Shaft 710 can be attached to socket 740, such as via threaded engagement or interference fit. Arcuate base 712 can rest flush against head 738. Sidewall 714 can extend proximally from arcuate base 712. Arcuate plate 716 can extend laterally from sidewall 714. Thus, arcuate track 742 can be located between arcuate base 712 and arcuate plate 716. As discussed with reference to FIG. 22, arcuate track 742 can be angled and offset relative to axis A14.

Arcuate knob 718 can be placed within arcuate track 742 to engage both arcuate base 712 and arcuate plate 716. Sidewall 720 can extend proximally from arcuate knob 718 and arcuate ledge 722 can extend laterally from sidewall 720 to extend over arcuate plate 716. The lower surface of arcuate ledge 722 can engage the upper surface of arcuate plate 716. The lower surface of arcuate plate 716 can engage the upper surface of arcuate knob 718. The lower surface of arcuate knob 718 can engage the upper surface of arcuate base 712. The arcuate surfaces can have the same center point to allow guide stem 706 to move in an arcuate pattern, as shown in FIG. 20B.

Arcuate knob 718 can permit guide stem 706 to uniplanarly articulate to allow cannulated reamer 750 (FIGS. 22 and 23) to change orientation relative to trial stem 702 such that axis A13 can change angles relative to axis A14. In particular, arcuate knob 718 can engage with arcuate base 712 and arcuate plate 716 to allow reamer guide stem 706 to move within an arcuate envelope. Specifically, the envelope can comprise a segment of a circle defined by the shape of arcuate track 742.

Arcuate guide path 744 can comprise a surface extending into and out of the plane of FIG. 20B having curvature that matches the curvature of arcuate base 712, arcuate knob 718, arcuate plate 716 and arcuate ledge 722. Due to the arcuate curvature of arcuate base 712, arcuate knob 718, arcuate plate 716 and arcuate ledge 722, the center of movement for guide stem 706 can be located at effective pivot point 746 below arcuate slide pad interface 703. Additionally, the curvature of slot 726 for pin 730 can match the curvature of arcuate base 712, arcuate knob 718, arcuate plate 716 and arcuate ledge 722.

In the example of FIGS. 20A-238, the effective pivot point of guide stem 706 can be lower relative to the examples of FIGS. 5-8 and 11A-11C. For example, the effective pivot point of the example of FIGS. 5-8 is where ball 126 is located directly between stem 124 and trial stem 110. Likewise, in the example of FIGS. 11A-11C, the effective pivot point is at pin 215. However, in the example of FIGS. 20A-23, effective pivot point 746 can be located at the center of curvature of arcuate base 712, arcuate knob 718, arcuate plate 716 and arcuate ledge 722. It can be desirable to have effective pivot point 746 further down along the length of elongate body 736 more closely match the shape of cannulated reamer 750, as shown in FIGS. 22 and 23. As such, angled reaming can be performed further down within tibia T (FIG. 2) to more closely match the angles of cortical bone within tibia T and without compromising the integrity of tibia T, e.g., without coming close to the exterior of cortical bone.

Figure 21B:
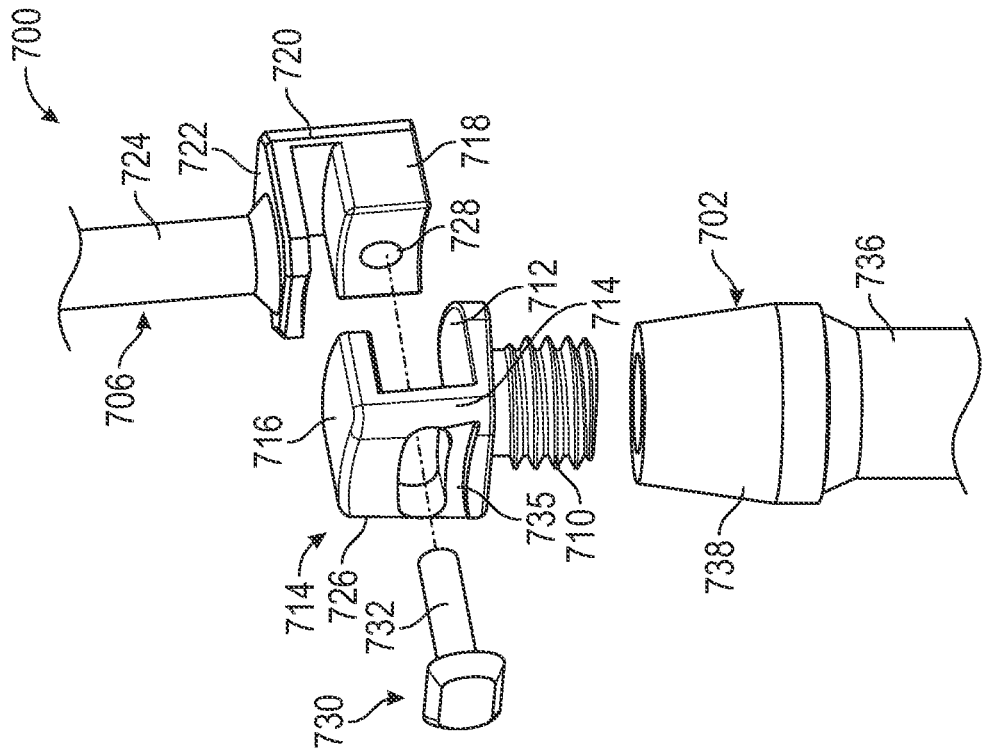
FIG. 21A and FIG. 21B are exploded views of the articulating guide device of FIGS. 20A-21B showing a coupler and a retainer.
Figure 21A:
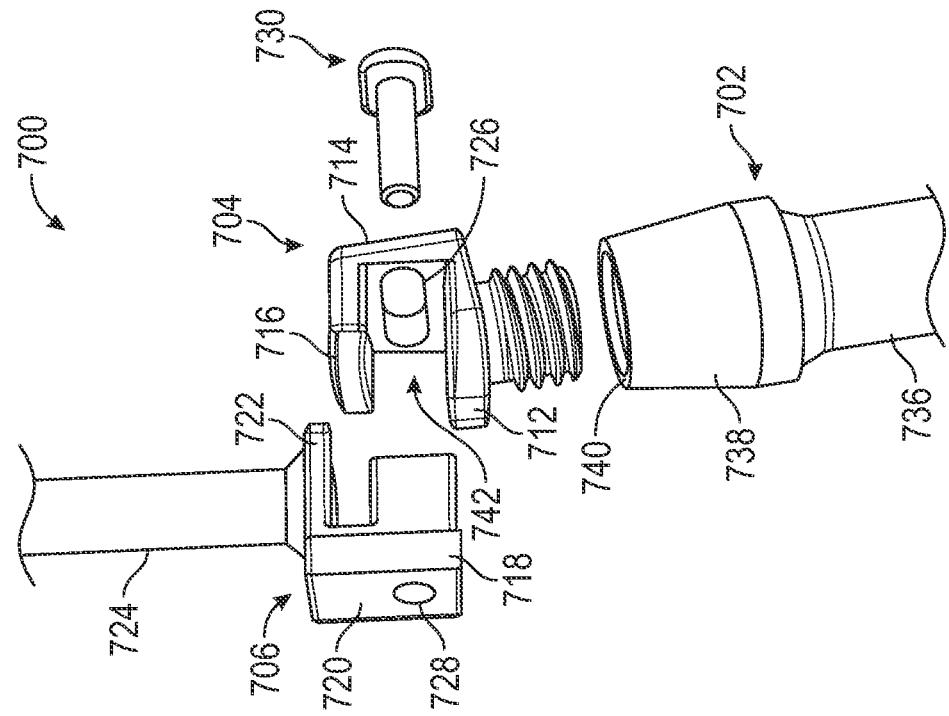

FIG. 21A and FIG. 21B are exploded views of articulating guide device 700 of FIGS. 20A and 20B showing cap 704 and guide stem 706. Pin 730 can be inserted into arcuate slot 726 and bore 728. Specifically, shaft 732 can be inserted through arcuate slot 726 and into bore 728. Shaft 732 can be secured to bore 728, such as via a threaded connection or interference fit. Head 734 can pull sidewall 714 toward sidewall 720. Head 734 can rest against ledge 735 when fully seated to prevent counter rotation of pin 730 relative to the direction of threading, for example. As such, guide stem 706 can remain engaged with cap 704. Shaft 732 can have a diameter approximately equal to the height of arcuate slot 726 to keep guide stem 706 and cap 704 aligned. Furthermore, arcuate knob 718 can be fit against surfaces of arcuate plate 716, sidewall 714 and arcuate base 712 to maintain guide stem 706 oriented relative to trial stem 702. However, the width of arcuate slot 726 can be smaller than the diameter of shaft 732 so that guide stem 706 can move along arcuate track 742 relative to cap 704.

FIG. 22 is a side view of articulating guide device 700 of FIGS. 20A-21B with cannulated reamer 750. FIG. 23 is a perspective view of articulating guide device 700 of FIG. 22 with cannulated reamer 750 shown in phantom over articulating guide device 700. Cannulated reamer 750 can be constructed similarly to other reamers described herein, such as cannulated reamer 114. Cannulated reamer 750 can slide along guidepost 724. Cannulated reamer 750 can comprise cannulated shaft 752 and cannulated cutter 754, which can include teeth. Cannulation 758 can extend through cannulated cutter 754 and into cannulated shaft 752. Cannulation 758 can include receptacle portion 760 that can fit over cap 704 and head 738 of trial stem 702.

Walls of cannulated cutter 754 can extend along lines L4 to form a trapezoidal bone-removal envelope. In examples, lines L4 can be configured to converge at or near effective pivot point 746. In additional examples, lines L4 can be configured to converge distal, e.g., further into the bone, of effective pivot point 746. As such, the curvatures of arcuate base 712, arcuate knob 718 and arcuate plate 716 and arcuate ledge 722 can be based on the angle between lines L4. Thus, the shape of cannulated cutter 754 can more closely match the shape of a cone or sleeve without having to extend arcuate slide pad interface 703 deep down into the bone.

As can be seen in FIG. 22, axis A13 of guidepost 724 of guide stem 706 can be angled relative to axis A14 of elongate body 736 of trial stem 702. Furthermore, axis A13 can be laterally offset from axis A14. Specifically, guidepost 724 can extend along axis A13, which can be disposed at angle α4 relative to axis A14 and can be offset distance D3 from axis A14. As discussed herein, angle α4 and distance D3 can be utilized to provide various complex shapes for bone pockets or envelopes configured to receive sleeves and cones.

FIG. 24 is a perspective view of system 800 comprising angled stem extension post 802 attached to trial stem 804. FIG. 25 is a cross-sectional view of system 800 of FIG. 24. FIGS. 24 and 25 are discussed concurrently.

Trial stem 804 can be constructed similarly as trial stem 202 described herein and can include elongate body 806 and head 808, which can include socket 810. Elongate body 806 can extend along axis A15. Angled stem extension post 802 can comprise coupler 812, shaft 814 and head 816. Shaft 814 can extend along axis A16. Angled stem extension post 802 can further comprise socket 818 and access port 820.

Angled stem extension post 802 can be attached to trial stem 804 to guide reaming along axis A16 at an angle to axis A15. Angled stem extension post 802 can be fastened to trail stem 804 via fastener 822, which can comprise shaft 824 and head 826. Faster 822 can immobilize angled stem extension post 802 relative to trial stem 804 so that a reaming operation can be performed without angled stem extension post 802 moving and adversely affecting the reaming operation. In particular, fastener 822 can restrain axial movement of angled stem extension post 802 along axis A15. However, as discussed below, angled stem extension post 802 can be allowed to rotate about fastener 822 along axis A15 to allow for alignment of angled stem extension post 802 relative to the tibia.

In examples, angled stem extension post 802 can be pre-assembled with trial stem 804 before trial stem 804 is inserted into bone. Fastener 822 can be attached to trial stem 804 by inserting shaft 824 into socket 810, such as be engaging mating threading. Fastener 822 can be fit radially through socket 818, such as via a force fit, to attach coupler 812 to fastener 822. Thus, coupler 812 can comprise a c-shaped body that wraps partially around shaft 824 underneath head 826. Socket 822 can have a profile shape of fastener 822 and a portion of head 808. Initially, fastener 822 can be tightened down such that head 826 is spaced from coupler 812. As such, angled stem extension post 802 can rotate about axis A15 as coupler 812 rotates about shaft 824. In additional examples, angled stem extension post 802 can be attached to trial stem 804 while trial stem 804 is inserted in bone. Socket 818 can comprise an opening in coupler 812 to allow angled stem extension post 802 to be moved onto and off of fastener 822. Socket 818 can comprise a T-shaped window that allows angled stem extension post 802 to be moved laterally, relative to axis A15, into engagement with head 826 of fastener 822.

Figure 26:
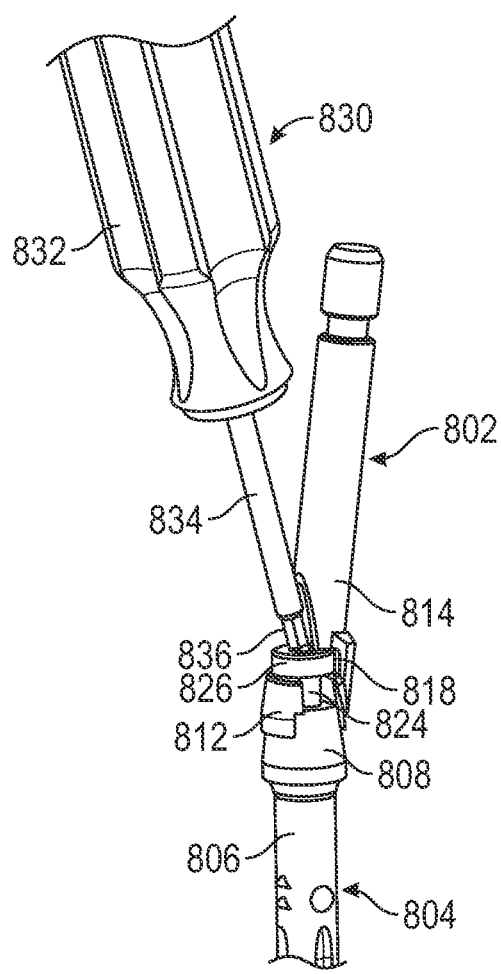
FIG. 26 is a perspective view of a driver instrument engaging a driver socket of the angled stem extension post of FIG. 24 to lock-down the angled stem extension relative to the trial stem.
Figure 27:
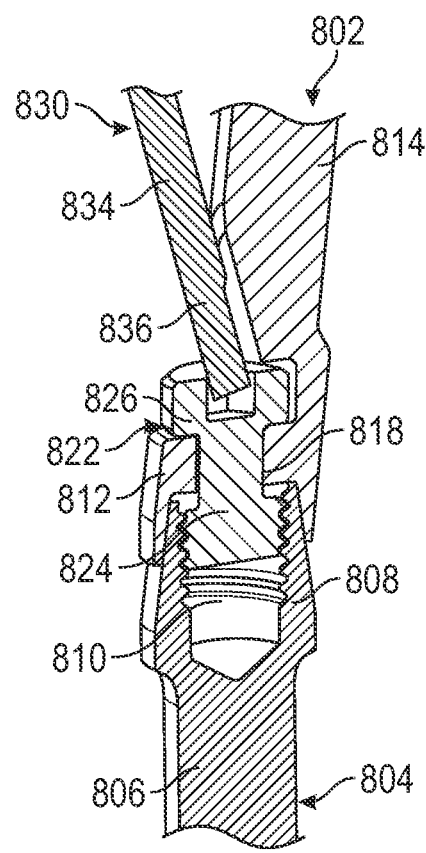
FIG. 27 is a cross-sectional view of the angled stem extension post, trial stem and driver instrument of FIG. 26.

FIG. 26 is a perspective view of driver instrument 830 inserted into access port 820 of the angled stem extension post 802 of FIG. 24. FIG. 27 is a cross-sectional view of angled stem extension post 802, trial stem 804 and driver instrument 830 of FIG. 26. Driver instrument 830 can comprise handle 832 and shaft 834. Shaft 834 can include tip 836. FIGS. 26 and 27 are discussed concurrently. Tip 836 of shaft 834 can comprise a hex head or other features that fit into a mating socket within head 826 to permit transfer of rotational force from driver instrument 830 to fastener 822. Tip 836 can extend into access port 820. Access port 820 can be formed by removal of material from shaft 814 that obstructs access to head 826 along axis A15. Access port 820 can intersect socket 818.

After both trial stem 804 is inserted into a tibia and angled stem extension post 802 is assembled to trial stem 808, a template device comprising handle 840 and template 842 can be attached to angled stem extension post 802 to provide alignment of angled stem extension post 802 relative to anatomy, as explained with reference to FIGS. 28 and 29, and, thereafter, fastener 822 can be tightened down to immobilize angled stem extension post 802 using driver device 830, as explained with reference to FIGS. 30 and 31.

Figure 28:
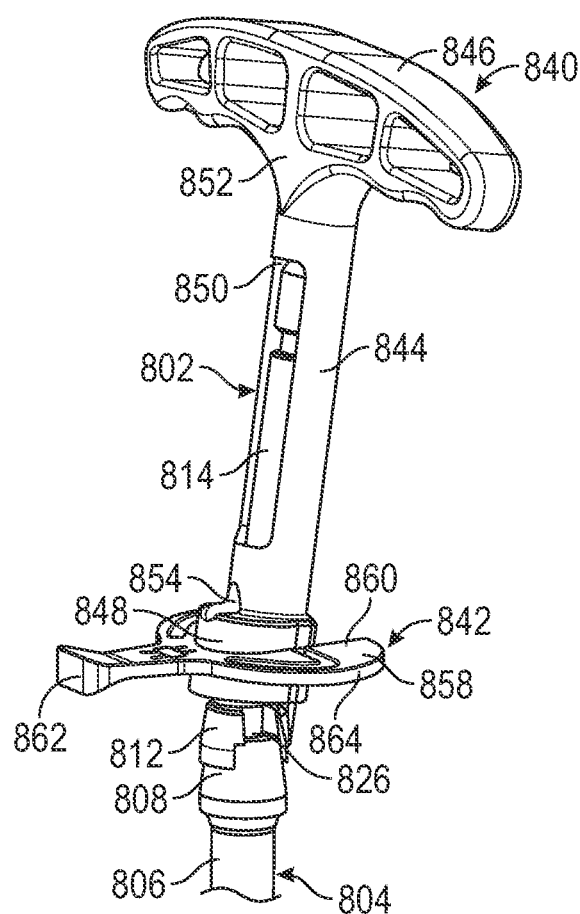
FIG. 28 is a perspective view of the angled stem extension post and trial stem of FIGS. 24-27 with a template attached to the template handle.

FIG. 28 is a perspective view of angled stem extension post 802 and trial stem 804 of FIGS. 24-27 with template handle 840 having template 842 attached to angled stem extension post 802. Template handle 840 can comprise shaft 844, grip 846 and head 848. Shaft 844 can comprise window 850 to allow for visual inspection of shaft 814 of angled stem extension post 802. Grip 846 can comprise features to facilitate handling of template 842. Grip 846 can extend along an axis that extends perpendicularly to shaft 844. Grip 846 can comprise front face 852 located on the same side of shaft 844 as window 850. Head 848 can include aperture 854 to allow for insertion of shaft 834 of driver instrument 830. Head 848 can also include track 856 (FIG. 30) for coupling with template 842. Template 842 can comprise body 858, slot 860 and extension 862. Track 856 can be configured to align template perpendicular to axis A15 (FIG. 24). Shaft 844 can be keyed to shaft 814 to allow handle 840 to slide over shaft 814 in only one relative rotational orientation. For example, the interior of head 848 can include cut-outs to sit atop coupler 812 in only one orientation. Furthermore, aperture 854 can be configured to align with access port 820. In examples, shaft 844 and shaft 814 can be keyed so that grip 846 extends in the medial-lateral direction when shaft 814 is angled posteriorly.

Figure 29:
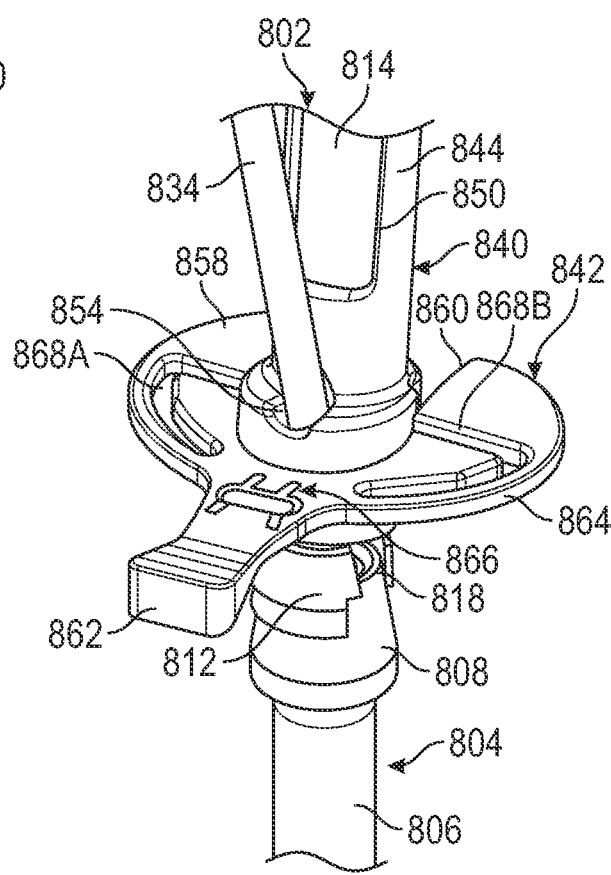
FIG. 29 is a close-up view of the template of FIG. 28 showing an outer perimeter of the template relative to alignment marks.

FIG. 29 is a close-up view of template 842 of FIG. 28 showing outer perimeter 864 of template 842 relative to alignment marks 866. Template 842 can further comprise windows 868A and 868B. Outer perimeter 864 can have the shape of a cone or sleeve configured to be positioned within a resected plane of a tibia. Thus, outer perimeter 864 can have medial and lateral curved sided with slot 860 being positioned therebetween on a posterior side. Extension 862 can be positioned the medial and lateral curved sides in an anterior location at a tibial tuberosity. Slot 860 can also allow template to be positioned on track 856 (FIG. 30). Alignment marks 866 can be provided to visualize where template 842 should be positioned relative to a tibial tuberosity. Extension 862 can also provide a grip to allow a surgeon a place to handle template 842. Windows 868A and 868B can be provided allow for visual inspection of bone underneath template 842. For example, windows 868A and 868B can be positioned to allow for viewing of a cortical bone wall. Additionally, windows 868A and 868B can be positioned to allow for visualization of where an implant to be positioned in the resected tibial surface is to be positioned.

Once template handle 840 and template 842 are attached to shaft 814 of angled stem extension post 802, grip 846 can be rotated to align template 842 in the desired location relative to the anatomy, such as when the tibial tuberosity is within alignment marks 866. A surgeon can therefore verify that outer perimeter 864 is adequately surrounded by cortical bone, so as to not be positioned outside of the tibia. If outer perimeter 864 is too close to cortical bone, grip 846 can be rotated clockwise or counterclockwise to move outer perimeter 864 within the cortical bene while keeping the tibial tuberosity within alignment marks 866.

Figure 30:
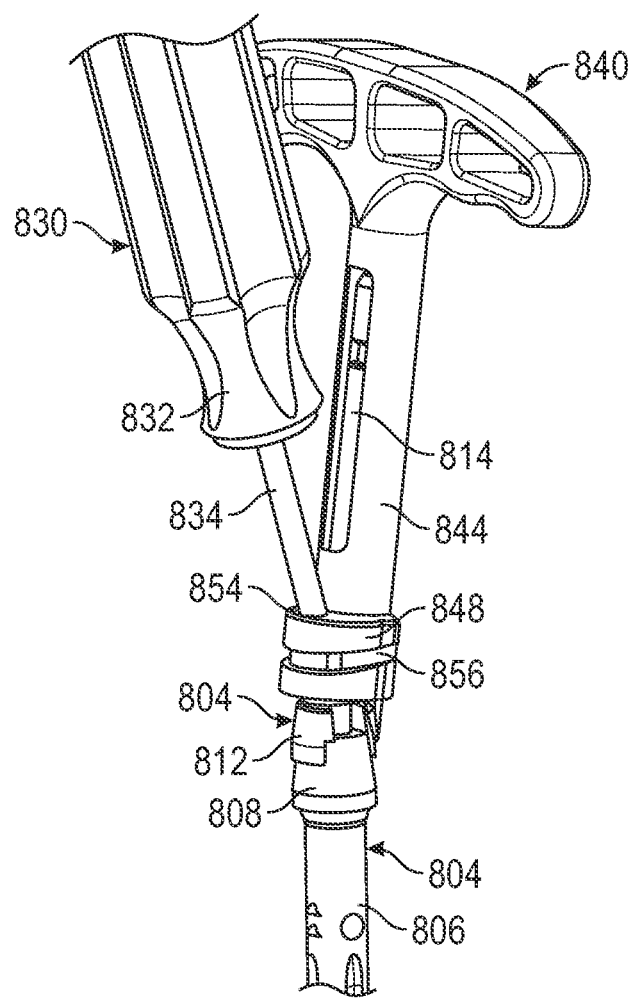
FIG. 30 is a perspective view of the angled stem extension post, trial stem and driver instrument of FIG. 29 with the template handle positioned over the angled stem extension.
Figure 31:
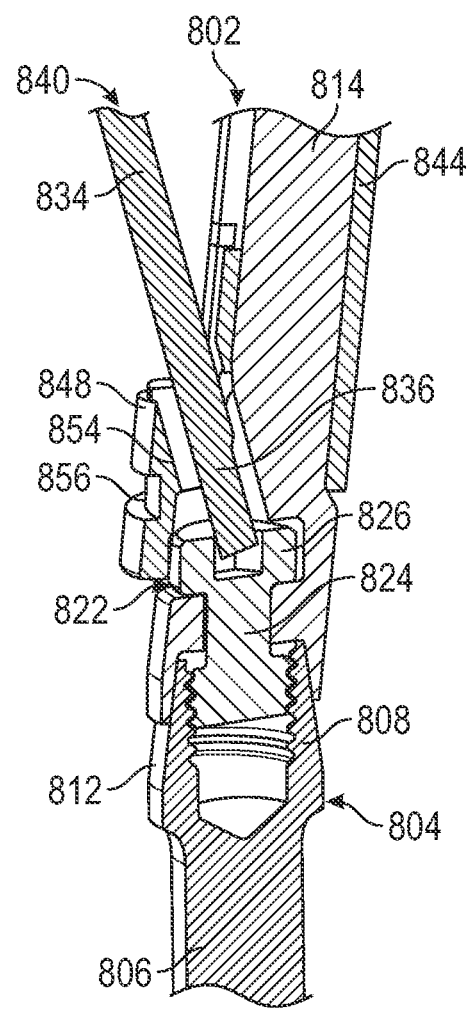
FIG. 31 is a cross-sectional view of the angled stem extension post, trial stem, driver instrument and template handle of FIG. 30.

FIG. 30 is a perspective view of angled stem extension post 802, trial stem 804 and driver instrument 830 of FIG. 29 with template handle 840 positioned over angled stem extension post 802. FIG. 31 is a cross-sectional view of angled stem extension post 802, trial stem 804, driver instrument 830 and template handle 840 of FIG. 30. Once template 842 is properly positioned as discussed above, a surgeon can know that reaming can be performed with angled stem extension post 802. Thus, driver instrument 830 can be inserted through aperture 854 and access port 820 to access fastener 822. Driver instrument 830 can then be rotated while engaged with head 826 to tighten fastener 822 down onto trial stem 804, thereby immobilizing angled stem extension post 802. Thereafter, a cannulated reamer, similar to cannulated reamer 750 of FIG. 23, for example, can be slid over shaft 814 of angled stem extension post 802 to ream a bone pocket within the resected tibial surface.

Figure 32:
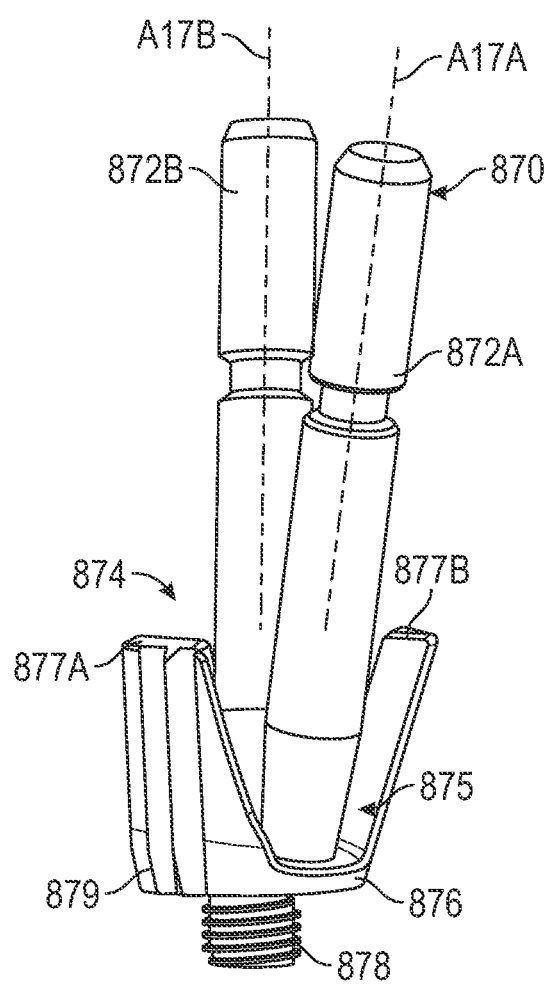
FIG. 32 is a perspective view of a secondary ream guide having two secondary ream posts that can be inserted into a bone socket produced with the devices of FIGS. 24-31.
Figure 33:
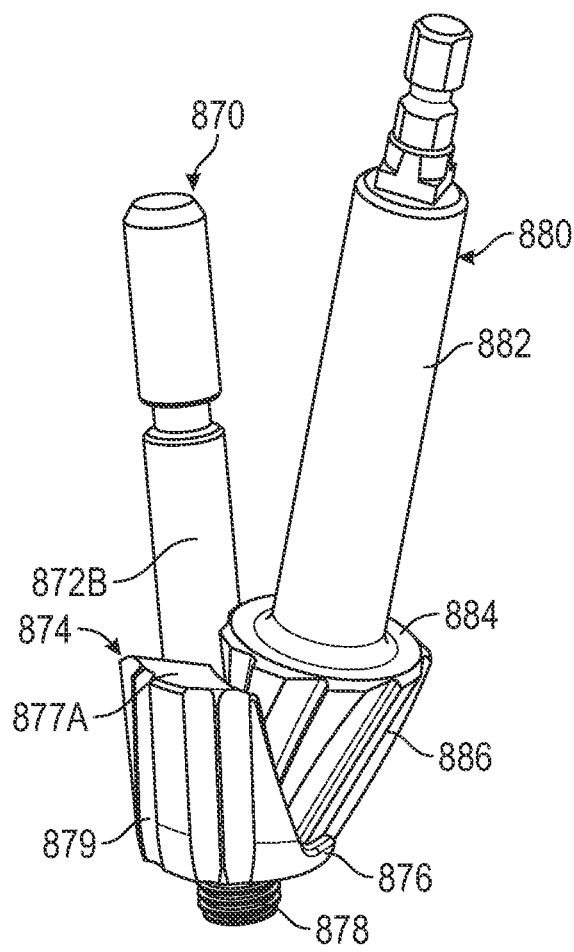
FIG. 33 is a perspective view of the secondary ream guide of FIG. 32 with a secondary reamer positioned over one of the secondary ream posts.

FIG. 32 is a perspective view of secondary ream guide 870 having first secondary ream post 872A and second secondary ream post 872B that can be inserted into a bone socket produced with the devices of FIGS. 24-31. Secondary ream guide 870 can comprise further comprise broach body 874, base 876 and extension 878. FIG. 33 is a perspective view of secondary ream guide 870 of FIG. 32 with secondary reamer 880 positioned over first secondary ream post 872A. Broach body 874 can include pocket 865 and teeth 879. Pocket 875 can interrupt the outer perimeter of broach body 874 to form anterior wall 877A and posterior wall 877B. Secondary reamer 880 can comprise cannulated shaft 882 and ream head 884, which can include teeth 886.

Trial stem 804 along with angled stem extension post 802 can be removed from the tibial. Broach body 874 can be positioned within a bone pocket formed by sliding cannulated reamer 750 (FIG. 23) over shaft 814. Broach body 874 can have a similar shape as cannulated cutter 754 of cannulated reamer 750, but with pocket 875 interrupting the outer perimeter shape. Broach body 874 can include teeth 879 to facilitate cutting into bone, e.g., displacing cancellous bone matter. Extension 878 can be connected to a stem that can be inserted into the space formed and vacated by stem 804 to provide stability. Secondary reamer 880 can be positioned over each of secondary ream posts 872A and 872B to form widening of the bone pocket formed by cannulated reamer 750. Cannulated shaft 882 can be positioned over each of secondary ream posts 872A and 872B in to perform sequential reaming operations using ream head 884. Ream head 884 can be cannulated to allow receiving of secondary ream posts 872A and 872B. Ream head 884 can be smaller than cannulated cutter 754 of cannulated reamer 750. Ream head 884 can fit into spaces within broach body 874 to allow for secondary reaming within the same apace as was performed with cannulated reamer 750. Thus, secondary ream posts 872A and 872B can help produce a complex reamed shape within the tibia. For example, ream head 884 can provide a different radius of curvature than cannulated cutter 754, such as by being smaller.

Additionally, ream head 884 can be provided along different axes, such as the axes 817A and 817B of secondary ream posts 872A an 872B that are at different angles than axis A16 relative to axis A15 (FIG. 24). Thus, secondary ream guide 870 can produce a multi-lobed bone pocket within the proximal tibial having outer walls disposed at different angles relative to axis A15, as evidenced by the protrusion of ream head 884 outside the perimeter of broach body 874. The angles of axis A16, A17A and A17B can be configured in different embodiments to match with different shaped cones and sleeves, thereby allowing such cones and sleeves to be engaged with cortical or healthy bone for different patients.

The present disclosure includes devices, systems and methods for reaming or otherwise modifying bone to produce various shaped sockets to receive prosthetic devices, such as cones and sleeves. The devices, systems and methods can produce complex shapes of precise dimensions to allow for precise removal of diseases or damaged bone, minimize removal of healthy bone, and allow for flush or tight fits between the modified bone and the prosthetic device when implanted. The devices, systems and methods can eliminate use of freehand reaming and minimize the use of complicated reaming mechanisms.

VARIOUS NOTES & EXAMPLES

Example 1 is a system for reaming an intramedullary canal of a long bone, the system comprising: a trial stem configured to extend into the long bone along an insertion axis; and a guide device comprising: an adapter configured to couple to the trial stem; and a reaming guidepost extending from the adapter along a guide axis; wherein the guide axis and the insertion axis are non-aligned.

In Example 2, the subject matter of Example 1 optionally includes wherein the reaming guidepost is in a fixed position relative to the adapter such that the insertion axis is offset from the guide axis.

In Example 3, the subject matter of Example 2 optionally includes wherein the insertion axis and the guide axis are parallel.

In Example 4, the subject matter of any one or more of Examples 2-3 optionally include wherein the insertion axis and the guide axis are oblique.

In Example 5, the subject matter of any one or more of Examples 1-4 optionally include wherein the reaming guidepost is rotatable relative to the adapter such that an angle between the insertion axis and the guide axis is variable.

In Example 6, the subject matter of Example 5 optionally includes wherein the reaming guidepost is pivotable in multiple directions relative to the adapter.

In Example 7, the subject matter of Example 6 optionally includes wherein the reaming guidepost is coupled to the adapter via a ball joint.

In Example 8, the subject matter of Example 7 optionally includes wherein the adapter comprises a socket from which the reaming guidepost extends, the socket comprising a perimeter defining an asymmetric shape.

In Example 9, the subject matter of any one or more of Examples 7-8 optionally include wherein the adapter comprises: a coupler comprising a threaded component configured to mate with the trial stem; and a limiter comprising: an attachment feature for attaching to the coupler; a sidewall extending from the attachment feature to define a chamber for receiving a ball of the ball joint, wherein the reaming guidepost extends from the ball; and a ledge extending from the sidewall to trap the ball within the chamber, the ledge overhanging the chamber to define an opening through which the reaming guidepost can extend.

In Example 10, the subject matter of any one or more of Examples 5-9 optionally include wherein the reaming guidepost is pivotable in a single plane relative to the adapter.

In Example 11, the subject matter of Example 10 optionally includes wherein the reaming guidepost is coupled to the adapter via a hinge device having a pivot pin that defines a pivoting point.

In Example 12, the subject matter of Example 11 optionally includes wherein the pivoting point is positioned outward of the trial stem.

In Example 13, the subject matter of any one or more of Examples 11-12 optionally include wherein the hinge device comprises a pair of flanges between which an eyelet of the reaming guidepost is disposed to receive the pivot pin, wherein the eyelet includes stop surfaces configured to limit pivoting of the reaming guidepost.

In Example 14, the subject matter of any one or more of Examples 10-13 optionally include wherein the reaming guidepost is coupled to the adapter via a slide device having a slide pin that defines a pivoting point.

In Example 15, the subject matter of Example 14 optionally includes wherein the pivoting point is positioned within the trial stem.

In Example 16, the subject matter of Example 15 optionally includes wherein the slide device comprises an arcuate track in which the slide pin is configured to move.

In Example 17, the subject matter of any one or more of Examples 10-16 optionally include wherein the guide axis is offset from the insertion axis.

In Example 18, the subject matter of any one or more of Examples 10-17 optionally include wherein the single plane in which the reaming guidepost pivots is angled relative to the insertion axis.

In Example 19, the subject matter of any one or more of Examples 1-18 optionally include an insertion tool configured to attach to the trial stem by sliding over the reaming guidepost; and an alignment device couplable to the insertion tool to indicate alignment of the reaming guidepost relative to the trial stem.

In Example 20, the subject matter of any one or more of Examples 1-19 optionally include a cannulated reamer configured to slide along the reaming guidepost.

Example 21 is a method of reaming an intramedullary canal of a long bone to form a complex shaped socket, the method comprising: inserting a stem into the intramedullary canal along an insertion axis; connecting a guide device to the stem, the guide device comprising a guidepost extending along a guide axis; and guiding a cannulated reamer along the guidepost to remove bone from the intramedullary canal to form the complex shaped socket; wherein the guide axis and the insertion axis are non-aligned.

In Example 22, the subject matter of Example 21 optionally includes wherein non-aligned comprises at least one of offset, angled, and pivotable relationships between the stem and the guidepost.

In Example 23, the subject matter of Example 22 optionally includes wherein non-aligned comprises at least two of offset, angled, and pivotable relationships between the stem and the guidepost.

In Example 24, the subject matter of any one or more of Examples 21-23 optionally include wherein guiding the cannulated reamer along the guidepost comprises guiding the cannulated reamer along a fixed guidepost.

In Example 25, the subject matter of Example 24 optionally includes wherein the fixed guidepost is offset relative to the stem.

In Example 26, the subject matter of Example 25 optionally includes wherein the fixed guidepost is parallel to the stem.

In Example 27, the subject matter of any one or more of Examples 25-26 optionally include wherein the fixed guidepost is angled relative to the stem.

In Example 28, the subject matter of any one or more of Examples 21-27 optionally include pivoting the guidepost relative to the stem using the cannulated reamer.

In Example 29, the subject matter of Example 28 optionally includes sweeping the cannulated reamer along an arc to move the cannulated reamer in a fixed vertical plane.

In Example 30, the subject matter of any one or more of Examples 28-29 optionally include articulating the cannulated reamer within a conical reaming envelope to move the cannulated reamer in a fixed horizontal plane.

In Example 31, the subject matter of Example 30 optionally includes moving the guidepost against a reaming template.

In Example 32, the subject matter of any one or more of Examples 28-31 optionally include engaging stops of the guidepost with the guide device to limit pivoting of the guidepost.

In Example 33, the subject matter of any one or more of Examples 21-32 optionally include connecting the guide device to the stem before inserting the stem into the intramedullary canal; sliding an insertion tool over the guidepost; and attaching the insertion tool to the stem.

In Example 34, the subject matter of Example 33 optionally includes positioning an alignment device attached to the insertion tool to rotationally align the guide device with long bone.

Example 35 is a system for reaming an intramedullary canal of a long bone, the system comprising: a trial stem configured to extend into the long bone along an insertion axis; and a guide device comprising: an adapter configured to couple to the trial stem; a reaming guidepost extending from the adapter along a guide axis; and a pivoting coupler connecting the reaming guidepost to the adapter; wherein the pivoting coupler produces a projected pivot point along the insertion axis spaced longitudinally from the adapter.

In Example 36, the subject matter of Example 35 optionally includes wherein the pivoting coupler comprises a spherical articulating interface.

In Example 37, the subject matter of Example 36 optionally includes wherein the spherical articulating interface comprises: a spherical plate on the adapter; and a spherical ledge on the reaming guidepost against which the spherical ledge is configured to slide.

In Example 38, the subject matter of Example 37 optionally includes wherein a center of curvature for the spherical plate and the spherical ledge are coincident with the projected pivot point.

In Example 39, the subject matter of any one or more of Examples 37-38 optionally include wherein the spherical plate comprises a template through which a post of the reaming guidepost extends.

In Example 40, the subject matter of Example 39 optionally includes wherein the template comprises a D-shaped oval.

In Example 41, the subject matter of any one or more of Examples 39-40 optionally include a spherical knob extending from the post of the reaming guidepost, wherein the spherical knob and the spherical ledge form a spherical socket in which the spherical plate is disposed.

In Example 42, the subject matter of Example 41 optionally includes wherein the adapter comprises: a coupler configured to engage the trial stem; and a limiter having the spherical plate; wherein the spherical knob is configured to be positioned between the coupler and the limiter.

In Example 43, the subject matter of any one or more of Examples 37-42 optionally include wherein the spherical plate and the spherical ledge have concentric spherical surfaces disposed about centerlines of the reaming guidepost and the trial stem, respectively.

In Example 44, the subject matter of any one or more of Examples 36-43 optionally include wherein an axis of the reaming guidepost is configured to coaxially align with an axis of the trial stem.

In Example 45, the subject matter of any one or more of Examples 35-44 optionally include wherein the pivoting coupler comprises an arcuate articulating interface.

In Example 46, the subject matter of Example 45 optionally includes wherein the arcuate articulating interface comprises: an arcuate plate on the adapter; and an arcuate ledge on the reaming guidepost against which the arcuate ledge is configured to slide.

In Example 47, the subject matter of Example 46 optionally includes wherein a center of curvature for the arcuate plate and the arcuate ledge are coincident with the projected pivot point.

In Example 48, the subject matter of any one or more of Examples 46-47 optionally include wherein the reaming guidepost comprises: a first sidewall extending from the arcuate ledge; and an arcuate knob extending from the first sidewall.

In Example 49, the subject matter of Example 48 optionally includes wherein the adapter comprises: a second sidewall extending from the arcuate plate; and an arcuate base extending from the second sidewall; wherein the arcuate base and the arcuate plate form an arcuate channel to receive the arcuate knob.

In Example 50, the subject matter of Example 49 optionally includes an arcuate channel in the second sidewall; a bore in the arcuate knob; and a pin configured to extend through the arcuate channel to engage the bore.

In Example 51, the subject matter of any one or more of Examples 46-50 optionally include wherein the arcuate plate and the arcuate ledge have concentric arcuate surfaces disposed about centerlines of the reaming guidepost and the trial stem, respectively.

In Example 52, the subject matter of any one or more of Examples 45-51 optionally include wherein an axis of the reaming guidepost is angled relative to an axis an axis of the trial stem in a direction separate from the arcuate articulating interface.

In Example 53, the subject matter of any one or more of Examples 45-52 optionally include wherein an axis of the reaming guidepost is offset from an axis of the trial stem.

In Example 54, the subject matter of any one or more of Examples 35-53 optionally include a reamer having a trapezoidal shaped reaming head, wherein angulation of the pivoting coupler corresponds to angles walls of the trapezoidal shaped reaming head.

Example 55 is a method of reaming an intramedullary canal of a long bone to form a complex shaped socket, the method comprising: inserting a stem into the intramedullary canal along an insertion axis; connecting a guide device to the stem, the guide device comprising a guidepost extending along a guide axis; guiding a cannulated reamer along the guidepost to remove bone from the intramedullary canal to form the complex shaped socket; and pivoting the guidepost relative to the stem with the cannulated reamer; wherein a projected pivot point along the insertion axis spaced longitudinally from the guide device along the insertion axis.

In Example 56, the subject matter of Example 55 optionally includes wherein pivoting the guidepost relative to the stem comprises moving the guidepost along an arcuate path in a spherical envelope.

In Example 57, the subject matter of Example 56 optionally includes wherein pivoting the guidepost relative to the stem comprises moving the guidepost three-hundred-sixty degrees about the insertion axis.

In Example 58, the subject matter of any one or more of Examples 56-57 optionally include wherein pivoting the guidepost relative to the stem comprises sliding a spherical plate of the guide device against a spherical ledge of the guidepost.

In Example 59, the subject matter of Example 58 optionally includes wherein pivoting the guidepost relative to the stem comprises engaging a post of the guidepost with a template in the spherical plate.

In Example 60, the subject matter of any one or more of Examples 55-59 optionally include wherein pivoting the guidepost relative to the stem comprises moving the guidepost along an arcuate path in a planar envelope.

In Example 61, the subject matter of Example 60 optionally includes wherein pivoting the guidepost relative to the stem comprises moving the guidepost back and forth across the insertion axis.

In Example 62, the subject matter of any one or more of Examples 60-61 optionally include wherein pivoting the guidepost relative to the stem comprises sliding an arcuate plate of the guide device against an arcuate ledge of the guidepost.

In Example 63, the subject matter of Example 62 optionally includes wherein pivoting the guidepost relative to the stem comprises sliding an arcuate knob of the guidepost with an arcuate channel of the guide device.

Example 64 is a system for reaming an intramedullary canal of a long bone, the system comprising: a trial stem configured to extend into the long bone along an insertion axis, an angled stem extension comprising: a shaft; and a coupler configured to rotatably attach the shaft to the trial stem at an angle to the insertion axis; and a fastener for selectively locking rotation of the angled stem extension relative to the trial stem.

In Example 65, the subject matter of Example 64 optionally includes wherein the fastener axially couples the angled stem extension to the trial stem.

In Example 66, the subject matter of Example 65 optionally includes wherein the fastener can be threadedly engaged with the trial stem to rotationally immobilize the angled stem extension.

In Example 67, the subject matter of any one or more of Examples 64-66 optionally include wherein the coupler includes a slot shaped to fit around a head of the fastener in a radial direction.

In Example 68, the subject matter of Example 67 optionally includes wherein the shaft includes a first aperture to allow access to the head of the fastener.

In Example 69, the subject matter of any one or more of Examples 64-68 optionally include a template device comprising: a handle configured to slide over the angled stem extension; and a template attached to the handle, the template having an outline of an implant to be inserted into the long bone.

In Example 70, the subject matter of Example 69 optionally includes wherein the handle comprises: a cannulated shaft; a grip located at a proximal end of the shaft; and a head located at a distal end of the shaft to which the template is attached.

In Example 71, the subject matter of Example 70 optionally includes wherein the shaft of the handle comprises: a second aperture configured to allow access to the fastener; and a window configured to allow viewing of the angled stem extension within the cannulated shaft.

In Example 72, the subject matter of any one or more of Examples 70-71 optionally include wherein: the grip extends perpendicular to the insertion axis; and the template is connected to the head so as to extend in a plane perpendicular to the insertion axis when the template device is attached to the angled stem extension.

In Example 73, the subject matter of any one or more of Examples 70-72 optionally include wherein the template includes markers configured to indicate a tolerance band for a portion of the template to be placed at the anterior-most point of the long bone.

In Example 74, the subject matter of any one or more of Examples 64-73 optionally include a secondary reaming guide comprising: a broach body configured to inserted into a bone pocket produced by a cannulated reamer sliding over the angled stem extension; a first angled broach guidepost extending from the broach body; and a second angled broach guidepost extending form the broach body; wherein the first and second angled broach guideposts extend in medial-posterior and lateral-posterior directions relative to the insertion axis, respectively.

Example 75 is a method of reaming an intramedullary canal of a long bone to form a bone pocket, the method comprising: inserting a stem into the intramedullary canal along an insertion axis; orienting an angled stem extension post relative to the stem; attaching a template to the angled stem extension post; rotating the template along with the angled stem extension to align the template with anatomic features of the long bone; locking a rotational position of the angled stem extension post relative to the stem; removing the template; and reaming the intramedullary canal along the angled stem extension.

In Example 76, the subject matter of Example 75 optionally includes wherein orienting the angled stem extension post relative to the stem comprises roughly aligning the angled stem extension toward a posterior side of the long bone.

In Example 77, the subject matter of any one or more of Examples 75-76 optionally include wherein rotating the template along with the angled stem extension to align the template with anatomic features of the long bone comprises positioning a perimeter of the template within an outer perimeter of the long bone.

In Example 78, the subject matter of any one or more of Examples 75-77 optionally include wherein attaching the template to the angled stem extension post further comprises: sliding a shaft of a template handle over the angled stem extension, wherein the template is attached to an exterior of the shaft.

In Example 79, the subject matter of Example 78 optionally includes wherein rotating the template along with the angled stem extension to align the template with anatomic features of the long bone comprises: rotating a grip attached to the shaft to extend in the medial-lateral direction relative to the long bone.

In Example 80, the subject matter of any one or more of Examples 75-79 optionally include wherein reaming the intramedullary canal along the angled stem extension comprises sliding a cannulated reamer along the angled stem extension to form the bone pocket in the long bone.

In Example 81, the subject matter of Example 80 optionally includes removing the stem along with the angled stem extension from the intramedullary canal, inserting a secondary ream guide into the bone pocket; and performing a secondary reaming operation using the secondary ream guide to modify the bone pocket.

In Example 82, the subject matter of Example 81 optionally includes wherein performing the secondary reaming operation using the secondary ream guide comprises: sliding a secondary reamer over a first guidepost of the secondary ream guide to widen the bone pocket in a medial direction; and sliding the secondary reamer over a second guidepost of the secondary ream guide to widen the bone pocket in a lateral direction.

In Example 83, the subject matter of any one or more of Examples 81-82 optionally include wherein the secondary ream guide comprises: a broach portion configured to broach the bone pocket; and first and second secondary ream guideposts extending from the broach portion; wherein the first and second secondary ream guideposts extend in medial-posterior and lateral-posterior directions relative to the insertion axis, respectively.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system for reaming an intramedullary canal of a long bone, the system comprising:
   a trial stem configured to extend into the long bone along an insertion axis;
   an angled stem extension comprising:
      a shaft; and
      a coupler configured to rotatably attach the shaft to the trial stem at an angle to the insertion axis;
   a fastener for selectively locking rotation of the angled stem extension relative to the trial stem; and
   a template device comprising:
      a handle configured to slide over the angled stem extension; and
      a template attached to the handle, the template having an outline of an implant to be inserted into the long bone.

2. The system of claim 1, wherein the fastener axially couples the angled stem extension to the trial stem.

3. The system of claim 2, wherein the fastener can be threadedly engaged with the trial stem to rotationally immobilize the angled stem extension.

4. The system of claim 1, wherein the coupler includes a slot shaped to fit around a head of the fastener in a radial direction.

5. The system of claim 4, wherein the shaft includes a first aperture to allow access to the head of the fastener.

6. The system of claim 1, wherein the handle comprises:
   a cannulated shaft;
   a grip located at a proximal end of the shaft; and
   a head located at a distal end of the shaft to which the template is attached.

7. The system of claim 6, wherein the shaft of the handle comprises:
   a second aperture configured to allow access to the fastener; and
   a window configured to allow viewing of the angled stem extension within the cannulated shaft.

8. The system of claim 6, wherein:
   the grip extends perpendicular to the insertion axis; and
   the template is connected to the head so as to extend in a plane perpendicular to the insertion axis when the template device is attached to the angled stem extension.

9. The system of claim 6, wherein the template includes markers configured to indicate a tolerance band for a portion of the template to be placed at the anterior-most point of the long bone.

10. The system of claim 1, further comprising a secondary reaming guide comprising:
    a broach body configured to inserted into a bone pocket produced by a cannulated reamer sliding over the angled stem extension;
    a first angled broach guidepost extending from the broach body; and
    a second angled broach guidepost extending form the broach body;
    wherein the first and second angled broach guideposts extend in medial-posterior and lateral-posterior directions relative to the insertion axis, respectively.

11. A method of reaming an intramedullary canal of a long bone to form a bone pocket, the method comprising:
    providing a system comprising:
       a trial stem configured to extend into the long bone along an insertion axis;
       an angled stem extension comprising:
          a shaft; and
          a coupler configured to rotatably attach the shaft to the trial stem at an angle to the insertion axis;
       a fastener for selectively locking rotation of the angled stem extension relative to the trial stem; and
       a template device comprising:
          a handle configured to slide over the angled stem extension; and a template attached to the handle, the template having an outline of an implant to be inserted into the long bone;
inserting the trial stem into the intramedullary canal along an insertion axis;
orienting the angled stem extension relative to the trial stem;
attaching a template to the angled stem extension;
rotating the template along with the angled stem extension to align the template with anatomic features of the long bone;
locking a rotational position of the angled stem extension relative to the trial stem;
removing the template; and
reaming the intramedullary canal along the angled stem extension.

12. The method of claim 11, wherein orienting the angled stem extension post relative to the stem comprises roughly aligning the angled stem extension toward a posterior side of the long bone.

13. The method of claim 11, wherein rotating the template along with the angled stem extension to align the template with anatomic features of the long bone comprises positioning a perimeter of the template within an outer perimeter of the long bone.

14. The method of claim 11, wherein attaching the template to the angled stem extension post further comprises:
sliding a shaft of a template handle over the angled stem extension, wherein the template is attached to an exterior of the shaft.

15. The method of claim 14, wherein rotating the template along with the angled stem extension to align the template with anatomic features of the long bone comprises:
rotating a grip attached to the shaft to extend in the medial-lateral direction relative to the long bone.

16. The method of claim 11, wherein reaming the intramedullary canal along the angled stem extension comprises sliding a cannulated reamer along the angled stem extension to form the bone pocket in the long bone.

17. The method of claim 16, further comprising:
removing the trial stem along with the angled stem extension from the intramedullary canal;
inserting a secondary ream guide into the bone pocket; and
performing a secondary reaming operation using the secondary ream guide to modify the bone pocket.

18. The method of claim 17, wherein performing the secondary reaming operation using the secondary ream guide comprises:
sliding a secondary reamer over a first guidepost of the secondary ream guide to widen the bone pocket in a medial direction; and
sliding the secondary reamer over a second guidepost of the secondary ream guide to widen the bone pocket in a lateral direction.

19. The method of claim 17, wherein the secondary ream guide comprises:
a broach portion configured to broach the bone pocket; and
first and second secondary ream guideposts extending from the broach portion;
wherein the first and second secondary ream guideposts extend in medial-posterior and lateral-posterior directions relative to the insertion axis, respectively.

20. A system for reaming an intramedullary canal of a long bone, the system comprising:
a trial stem configured to extend into the long bone along an insertion axis;
an angled stem extension comprising:
a shaft; and
a coupler configured to rotatably attach the shaft to the trial stem at an angle to the insertion axis;
a fastener for selectively locking rotation of the angled stem extension relative to the trial stem; and
a secondary reaming guide comprising:
a broach body configured to inserted into a bone pocket produced by a cannulated reamer sliding over the angled stem extension;
a first angled broach guidepost extending from the broach body; and
a second angled broach guidepost extending form the broach body;
wherein the first and second angled broach guideposts extend in medial-posterior and lateral-posterior directions relative to the insertion axis, respectively.

* * * * *